United States Patent [19]

Hemmi et al.

[11] Patent Number: 5,538,950
[45] Date of Patent: Jul. 23, 1996

[54] ENDOTHELIN ANTAGONISTS AND THEIR PREPARATION

[75] Inventors: Keiji Hemmi, Tsukuba; Masahiro Neya, Tsuchiura; Naoki Fukami, Ibaraki; Masashi Hashimoto, Toride; Hirokazu Tanaka, Tsuchiura; Natsuko Kayakiri, Tsukuba, all of Japan

[73] Assignee: Fujisawa Pharmaceutical Co., Ltd., Osaka, Japan

[21] Appl. No.: 232,156

[22] PCT Filed: Oct. 30, 1992

[86] PCT No.: PCT/JP92/01405

§ 371 Date: May 12, 1994

§ 102(e) Date: May 12, 1994

[87] PCT Pub. No.: WO93/10144

PCT Pub. Date: May 27, 1993

[30] Foreign Application Priority Data

Nov. 12, 1991 [GB] United Kingdom ............. 9123967

[51] Int. Cl.$^6$ .................. A61K 37/02; C07K 5/08
[52] U.S. Cl. ............... 514/18; 514/19; 544/62; 544/143; 544/373; 546/168; 546/201; 546/256; 546/14; 546/277.4; 546/278.1; 548/455; 548/496; 530/331; 540/481; 540/597; 540/598; 540/583

[58] Field of Search ............ 514/18, 19; 540/480, 540/602; 544/62, 143, 373; 546/168, 201, 273; 548/455, 496; 530/331

[56] References Cited

U.S. PATENT DOCUMENTS 5,284,828  2/1994  Hemmi et al. .............. 514/18
5,321,032  6/1994  Matsuo et al. ............. 514/308

FOREIGN PATENT DOCUMENTS 333174   9/1989   European Pat. Off. .
457195   11/1991  European Pat. Off. .
9112266  8/1991   WIPO .

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

A compound of the formula:

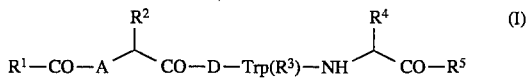

in which $R^3$ is hydrogen or lower alkyl,
$R^4$ is pyridyl (lower) alkyl; and
$R^1$, $R^2$, $R^5$ and A are defined in the description;
or a pharmaceutically acceptable salt thereof, which have endothelin antagonistic activity.

24 Claims, No Drawings

ENDOTHELIN ANTAGONISTS AND THEIR PREPARATION

This application is the national phase, filed under 37 C.F.R. 1.371 of PCT/JP92/01405, filed Oct. 30, 1992.

The present invention relates to new compound and a pharmaceutically acceptable salt thereof.

More particularly, it relates to new peptide compound and a pharmaceutically acceptable salt thereof which have pharmacological activities such as endotheline antagonistic activity and the like, to processes for its preparation, to a pharmaceutical composition comprising the same, and to a method of using the same therapeutically in the treatment and the prevention of endothelin mediated diseases such as hypertension, and the like.

One object of the present invention is to provide new and useful peptide compound and a pharmaceutically acceptable salt thereof which have pharmacological activities such as endothelin antagonistic activity and the like.

Another object of the present invention is to provide processes for the preparation of said peptide compound and a salt thereof.

A further object of the present invention is to provide a pharmaceutical composition comprising, as an active ingredient, said peptide compound or a pharmaceutically acceptable salt thereof.

Still further object of the present invention is to provide a method of using the same for the treatment and the prevention of endothelin mediated diseases such as hypertension, and the like.

DISCLOSURE OF INVENTION

The object compound of the present invention can be represented by the following general formula (I).

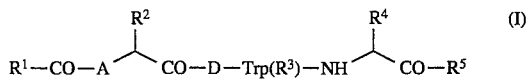

in which $R^3$ is hydrogen or lower alkyl,
$R^4$ is pyridyl(lower)alkyl; and
$R^1$ is $C_3$–$C_8$alkyleneamino, N,N-di(lower)alkylamino, N-lower alkyl-N-arylamino, N-lower alkyl-N-$C_3$–$C_8$cycloalkylamino, or $C_5$–$C_{10}$bicyclic alkyleneamino,
$R^2$ is lower alkyl,
$R^5$ is $C_3$–$C_8$alkyleneamino, N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, $C_3$–$C_8$alkyleneamino(lower)alkylamino which may be substituted by oxo, or pyridyl(lower)alkylamino, and
A is lower alkylene; or
$R^1$ is piperidin-1-yl, lower alkylpiperidin-1-yl, octahydroazocin-1-yl, indolin-1-yl, 1,2,3,4-tetrahydroquinolin-1-yl, N,N-di(lower)alkylamino, N-lower alkyl-N-arylamino, N-lower alkyl-N-$C_3$–$C_8$cycloalkylamino, or $C_5$–$C_{10}$bicyclic alkyleneamino,
$R^2$ is lower alkyl,
$R^5$ is amino or lower alkylamino, and
A is lower alkylene; or
$R^1$ is piperidin-1-yl, octahydroazocin-1-yl, N,N-di(lower)alkylamino, or $C_5$–$C_{10}$bicyclic alkyleneamino,
$R^2$ is lower alkyl,
$R^5$ is amino, lower alkylamino, N,N-di(lower)alkylamino, $C_3$–$C_8$alkyleneamino, or morpholino, and
A is —NH—; or
$R^1$ is hexahydro-1H-azepin-1-yl,
$R^2$ is isobutyl,
$R^5$ is ethylamino, and
A is methylene; or
$R^1$ is N-[1-(dimethylcarbamoyl)-2,2-dimethylpropyl]amino,
$R^2$ is isobutyl,
$R^5$ is amino, and
A is —NH—; or
$R^1$ is N,N-di(lower)alkylamino, 1,2,3,4-tetrahydroquinolin-1-yl, N-lower alkyl-N-arylamino, or N-lower alkyl-N-$C_3$–$C_8$cycloalkylamino,
$R^2$ is lower alkyl,
$R^5$ is hydroxy or CO—$R^5$ is protected carboxy, and
A is lower alkylene; or
$R^1$ is $C_5$–$C_{10}$bicyclic alkyleneamino,
$R^2$ is lower alkyl,
$R^5$ is hydroxy or CO—$R^5$ is protected carboxy, and
A is lower alkylene or —NH—; or
$R^1$ is N-ethyl-N-(1-ethylpropyl)amino, N-ethyl-N-isopropylamino, N-ethyl-N-neopentylamino, or N-(1-ethylpropyl)-N-propylamino,
$R^2$ is isobutyl,
$R^5$ is hydroxy or CO—$R^5$ is protected carboxy, and
A is —NH—; or
$R^1$ is piperidin-1-yl,
$R^2$ is isobutyl,
$R^5$ is hydroxy or CO—$R^5$ is protected carboxy, and
A is methylene; or
$R^1$ is hexahydro-1H-azepin-1-yl,
$R^2$ is propyl,
$R^5$ is hydroxy or CO—$R^5$ is protected carboxy, and
A is —NH—;
or a pharmaceutically acceptable salt thereof.

Particularly, the compound represented by the following formula (I') is more useful as an endothelin antagonist and the like.

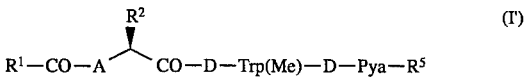

in which $R^1$, $R^2$, $R^5$ and A are each as defined above.

Suitable examples of each definition for the compound (I) may be exemplified by the preferred embodiments of the compound (I) mentioned below.

Preferred embodiments of the definitions of the compound (I) may be:

$R^2$ is isobutyl, $R^5$ is pyrrolidin-1-yl, A is methylene, and $R^1$ is piperidino, hexahydro-1H-azepin-1-yl, octahydroazocin-1-yl, N-methyl-N-cyclohexylamino, N-ethyl-N-isopropylamino, N-propyl-N-(1-ethylpropyl)amino, N-ethyl-N-(1-ethylpropyl)amino, 3-azabicyclo[3.2.2]nonan- 3-yl or N-neopentyl-N-ethylamino; or $R^2$ is isobutyl $R^5$ is pyrrolidin-1-yl, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan- 3-yl or N-neopentyl-N-ethylamino; or $R^2$ is isobutyl, $R^5$ is dimethylamino, A is methylene, and $R^1$ is piperidino, hexahydro-1H-azepin-1-yl, octahydroazocin-1-yl, N-methyl-N-phenylamino, N-methyl-N-cyclohexylamino, N-ethyl-N-isopropylamino, N-propyl-N-(1-ethylpropyl)amino, 3-azabicyclo[3.2.2]nonan-3-yl, N-neopentyl-N-ethylamino or N-methyl-N-(o-tolyl)amino; or $R^2$ is isobutyl, $R^5$ is dimethylamino, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan-3-yl, or N-neopentyl-N-ethylamino; or $R^2$ is isobutyl, $R^5$ is ethylamino, A is —NH—, and $R^1$ is piperidino or octahydroazocin-1-yl; or $R^1$ is hexahydro-1H-azepin-1-yl, $R^2$ is isobutyl, $R^5$ is ethylamino and A is methylene; or $R^2$ is isobutyl, $R^5$ is morpholino, A is methylene, and $R^1$ is piperidino, hexahydro-1H-azepin-1-yl, octahydroazocin-1-yl or N-methyl-N-cyclohexylamino; or $R^2$ is isobutyl, $R^5$ is morpholino, A is —NH—, and $R^1$ is piperidino, octahydroazocin-1-yl or N-ethyl-N-(1-ethylpropyl)amino; or $R^1$ is hexahydro-1H-azepin-1-yl, $R^2$ is isobutyl, A is methylene, and $R^5$ is thiomorpholino, piperidino, N',N'-dimethylhydrazino, morpholinoamino, 4-methylpiperazin-1-ylamino, ethylamino, 2-methoxyethylamino, 2-morpholinoethylamino, 3-(2-oxopyrrolidin-1-yl)propylamino, 2-piperidinoethylamino or 2-(pyridin-2-yl)ethylamino; or $R^2$ is isobutyl, $R^5$ is amino, A is methylene, and $R^1$ is piperidino, octahydroazocin-1-yl, dipropylamino, N-methyl-N-butylamino, N-ethyl-N-butylamino, N-ethyl-N-isopropylamino, N-ethyl-N-(1-ethylpropyl)amino, N-propyl-N-(1-ethylpropyl)amino, 3-azabicyclo[3.2.2]nonan-3-yl, N-ethyl-N-neopentylamino, N-methyl-N-cyclohexylamino, N-methyl-N-phenylamino, 1,2,3,4-tetrahydroquinolin-1-yl, 4-methylpiperidino or indolin-1-yl; or $R^2$ is isobutyl, $R^5$ is amino, A is —NH—, and $R^1$ is piperidino, octahydroazocin-1-yl, N-ethyl-N-(1-ethylpropyl)amino, N-propyl-N-(1-ethylpropyl)amino, N-ethyl-N-neopentylamino, (1-dimethylcarbamoyl-2,2-dimethylpropyl)amino or 3-azabicyclo[3.2.2]nonan-3-yl;

$R^2$ is isobutyl, $R^5$ is methylamino, A is —NH—, and $R^1$ is piperidino, octahydroazocin-1-yl, N-ethyl-N-neopentylamino or 3-azabicyclo[3.2.2]nonan-3-yl; or $R^2$ is isobutyl, $R^5$ is methylamino, A is methylene, and $R^1$ is piperidino, octahydroazocin-1-yl or N-methyl-N-cyclohexylamino;

$R^2$ is isobutyl, $R^5$ is hydroxy, A is methylene, and $R^1$ is piperidino, N-ethyl-N-isopropylamino, N-propyl-N-(1-ethylpropyl)amino, N-ethyl-N-(1-ethylpropyl)amino or 3-azabicyclo[3.2.2]nonan-3-yl; or $R^2$ is isobutyl, $R^5$ is hydroxy, A is —NH—, and $R^1$ is N-ethyl-N-isopropylamino, N-propyl-N-(1-ethylpropyl)amino, N-ethyl-N-(1-ethylpropyl)amino or 3-azabicyclo [3.2.2 ]-nonan-3-yl; or $R^1$ is hexahydro-1H-azepin-1-yl, $R^2$ is propyl, $R^5$ is hydroxy and A is —NH—; or $R^2$ is isobutyl, $R^5$ is ethoxy, A is methylene, and $R^1$ is piperidino, N-methyl-N-cyclohexylamino, N-methyl-N-phenylamino, N-ethyl-N-isopropylamino, N-propyl-N-(1-ethylpropyl)amino, N-ethyl-N-(1-ethylpropyl)amino, 3-azabicyclo[3.2.2]nonan-3-yl or 1,2,3,4-tetrahydroquinolin-1-yl; or $R^2$ is isobutyl, $R^5$ is ethoxy, A is —NH—, and $R^1$ is N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino; or $R^1$ is hexahydro-1H-azepin-1-yl, $R^2$ is propyl, $R^5$ is ethoxy and A is —NH—.

According to the present invention, the new peptide compound (I) and a salt thereof can be prepared by the processes as shown in the following schemes.

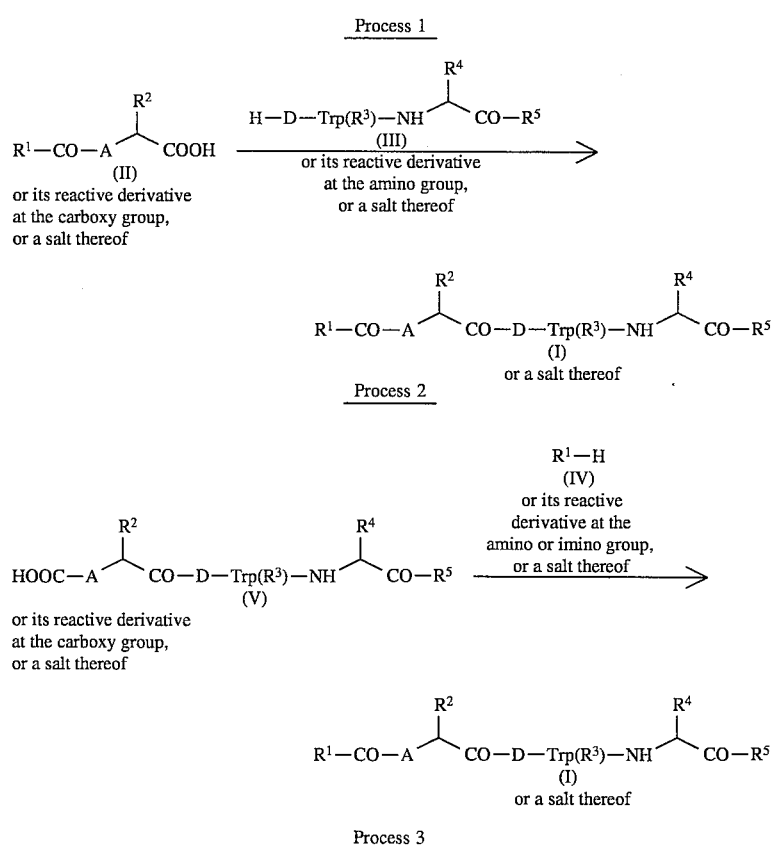

Process 1

Process 2

Process 3

-continued

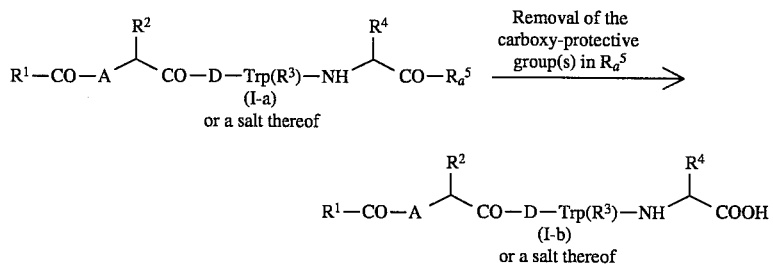

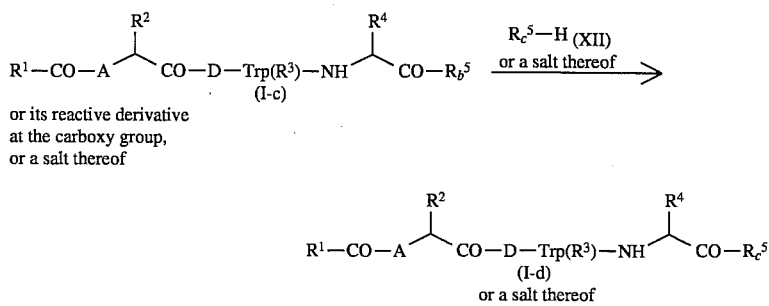

in which $R^1$, $R^2$, $R^3$, $R^4$, $R^5$ and A are each as defined above,
CO—$R_a^5$ is protected carboxy,
CO—$R_b^5$ is carboxy or protected carboxy, and
$R_c^5$ is $C_3$—$C_8$alkyleneamino N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, $C_3$–$C_8$alkyleneamino(lower)alkylamino which may be substituted by oxo, pyridyl(lower)alkylamino, amino or lower alkylamino.

Some of the starting compounds used in the above Processes are novel and can be prepared according to the following Methods and/or by the procedures described in the following Preparations or by a conventional manner.

Method 1

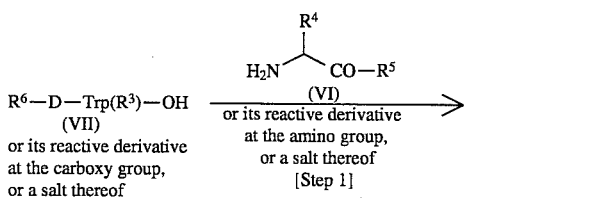

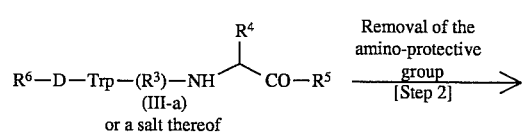

Method 2

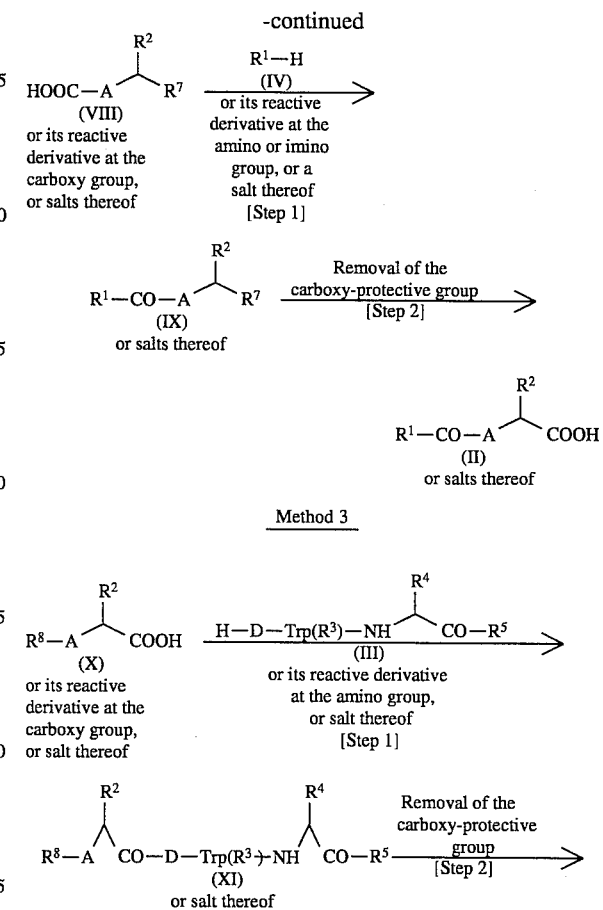

-continued

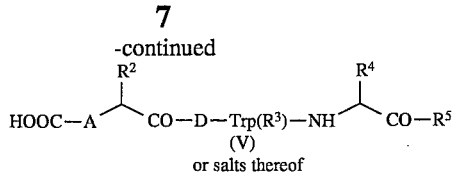
(V)
or salts thereof in which $R^1$, $R^2$, $R^3$, $R^4$, $R^5$ and A are each as defined above,
$R^6$ is amino-protective group,
$R^7$ is protected carboxy, and
$R^8$ is protected carboxy.

Throughout the present specification, the amino acids, peptides, protective groups, condensing agents, etc. are indicated by the abbreviations according to the IUPAC-IUB (Commission on Biological Nomenclature) which are in common use in a field of this art.

Moreover, unless otherwise indicated, the amino acids and their residues when shown by such abbreviations are meant to be L-configured compounds and residues, while the D-configured compounds and residues are shown with the prescript of D-.

Suitable pharmaceutically acceptable salts of the object compound (I) may be a conventional non-toxic salt and include an acid addition salt such as an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with a base such as an amino acid (e.g. arginine, aspartic acid, glutamic acid, etc.), an alkali metal salt (e.g. sodium salt, potassium salt, etc.), an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention includes within the scope thereof are explained in detail as follows.

The term "lower" is intended to mean 1 to 6, preferably 1 to 5 carbon atoms, unless otherwise indicated.

Suitable "amino-protective group" may include acyl such as an aliphatic acyl, an aromatic acyl, a heterocyclic acyl and an aliphatic acyl substituted with aromatic or heterocyclic group(s) derived from acid such as carboxylic, carbonic, carbamic, sulfonic acids.

Preferable "amino-protective group" thus defined may be the ones usually used in the peptide chemistry, such as t-butoxycarbonyl, and the like.

Suitable "protected carboxy" for CO—$R^5$ may include esterified carboxy mentioned below.

Preferable "esterified carboxy" can be referred to the ones usually used in the peptide chemistry, such as lower alkoxycarbonyl, and the like.

The processes for preparing the object compound (I) are explained in detail in the following.

PROCESS 1

The object compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

Suitable salts of the compound (III) and its reactive derivative can be referred to the acid addition salts as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxilic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminiomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

Suitable salts of the compound (II) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.] or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carboxiimide; N,N'-diethylcarbodiimide, N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 2

The object compound (I) or a salt thereof can be prepared by reacting the compound (V) or its reactive derivative at the carboxy group, or a salt thereof with the compound (IV) or its reactive derivative at the amino or imino group, or a salt thereof.

Suitable salts of the compound (I) and its reactive derivative can be referred to the ones as exemplified for the compound (III) and the compound (II), respectively.

Suitable reactive derivative of the compound (IV) can be referred to the ones as exemplified for the compound (III).

Suitable salts of the compound (IV) can be referred to acid addition salts as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

PROCESS 3

The object compound (I-b) or a salt thereof can be prepared by subjecting the compound (I-a) or a salt thereof to removal reaction of the carboxy-protective group in $R_a^5$.

Suitable salts of the compounds (I-a) and (I-b) can be referred to the ones as exemplified for the compound (I).

This reaction is carried out in accordance with a conventional method such as solvolysis including hydrolysis, reduction or the like.

The solvolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate, or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.].

The removal reaction using Lewis acid such as trihaloacetic acid [e.g. trichloroacetic acid, trifluoroacetic acid, etc.] or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, carbon tetrachloride, tetrahydrofuran, N,N-dimethylformamide, a mixture thereof or any other solvent which does not adversely influence the reaction. A liquid base or acid can be also used as the solvent. The reaction temperature is not critical and the reaction is usually carried out under cooling to heating.

The reduction method applicable for the removal reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

PROCESS 4

The object compound (I-d) or a salt thereof can be prepared by reacting the compound (I-c) or its reactive derivative at the carboxy group, or a salt thereof with the compound (XII), or a salt thereof.

Suitable salts of the compound (I-c) and its reactive derivative can be referred to the ones as exemplified for the compound (I) and the compound (II), respectively.

Suitable salts of the compound (I-d) can be referred to the ones as exemplified for the compound (I).

Suitable salts of the compound (XII) may be acid addition salts as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

The compounds obtained by the above processes can be isolated and purified by a conventional method such as pulverization, recrystallization, column chromatography, reprecipitation, or the like.

The object compound (I) can be transformed into its salt in a conventional manner.

The method for preparing the new starting compounds are explained in detail in the following.

METHOD 1

[Step 1]

The compound (III-a) or a salt thereof can be prepared by reacting the compound (VII) or its reactive derivative at the carboxy group, or a salt thereof with the compound (VI) or its reactive derivative at the amino group, or a salt thereof.

Suitable salts of the compound (VII) and its reactive derivative can be referred to the ones as exemplified for the compound (II).

Suitable salts of the compound (VIII) and its reactive derivative can be referred to the ones as exemplified for the compound (III).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

[Step 2]

The compound (III) or a salt thereof can be prepared by subjecting the compound (III-a) or a salt thereof to a removal reaction of the amino-protective group of $R^6$ in a conventional manner such as those explained in Process 3.

METHOD 2

[Step 1]

The compound (IX) or a salt thereof can be prepared by reacting the compound (VIII) or its reactive derivative at the carboxy group, or a salt thereof with the compound (IV) or its reactive derivative at the amino or imino group, or a salt thereof.

Suitable salts of the compound (VIII) or its reactive derivative can be referred to the ones as exemplified for the compound (II).

In case that the symbol "A" is —NH—, the reactive derivative of the compound (VIII) may also include isocyanates thereof.

Suitable salts of the compound (IX) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

[Step 2]

The compound (II) or a salt thereof can be prepared by subjecting the compound (IX) or a salt thereof to a removal reaction of the carboxy-protective group on $R^7$ in a conventional manner such as those explained in Process 3.

Suitable salts of the compound (II-a) may be the same as those for the compound (II).

METHOD 3

[Step 1]

The compound (XI) or a salt thereof can be prepared by reacting the compound (X) or its reactive derivative at the carboxy group, or a salt thereof with the compound (III) or its reactive derivative at the amino group, or a salt thereof.

Suitable salts of the compound (X) or its reactive derivative can be referred to the ones as exemplified for the compound (II).

Suitable salts of the compound (XI) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

[Step 2]

The compound (V) or a salt thereof can be prepared by subjecting the compound (XI) or a salt thereof to a removal reaction of the carboxy-protective group on $R^8$ in a conventional manner such as those explained in Process 3.

It is to be noted that the compound (I) and the other compounds may include one or more stereoisomers due to asymmetric carbon atoms, and all of such isomers and mixture thereof are included within the scope of this invention.

The object compound (I) and a pharmaceutically acceptable salt thereof have pharmacological activities such as endothelin antagonistic activity, for example, relaxating activity of blood vessel, and the like, and useful for therapeutical treatment and prevention of endothelin mediated diseases such as hypertension, heart disease such as angina pectoris, cardiomyopathy, myocardial infarction or the like, cerebral stroke such as cerebral arterial spasm, cerebral ischemia, cerebrovascular twitch or the like, late phase cerebral spasm after subarachnoid hemorrhage, asthma such as bronchoconstriction or the like, renal failure such as acute renal failure, renal insufficiency caused by pharmaceuticals (e.g. Cisplatin, Cyclosporins, etc.), peripheral circulatory failure, such as Raynaud's disease, Buerger's disease, etc., arteriosclerosis, diabetic nephropathy, diabetic retinopathy, shock such as hemorrhagic shock, shock induced by endotoxins, etc., hemangioendothelioma, organopathy after reperfusion [e.g. after organ and tissue transplantation, percutaneous transluminal coronary angiopathy (PTCA), or percutaneous transluminal coronary recanalization (PTCR), etc.], bloodstream disturbance after an operation, ulcer, irritable bowel syndrome (IBS), dysuria, retionopathy, dysmenorrheal, premature birth such as premature labor, threatened abortion, or the like, glaucoma, re-occlusion after operation of PTCA, and the like.

For therapeutic purpose, the peptide compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration.

Especially, the peptide compound (I) of this invention is suitable for oral administration.

The pharmaceutical preparations may be capsules, tablets, dragees, granules, solution, suspension, emulsion, sublingual tablet, suppositories, ointment, aerosol, infusion, ophthalmic solutions, vaginal suppository, and the like. If desired, there may be included in these preparations, auxiliary substances, stabilizing agents, wetting or emulsifying agents, buffers and other commonly used additives.

While the dosage of the compound (I) will vary depending upon the age and condition of the patient, in the case of intravenous administration, a daily dose of 0.01–100 mg of the active ingredient per kg weight of human being, in the case of intramuscular administration, a daily dose of 0.05–100 mg of the same per kg weight of human being, in case of oral administration, a daily dose of 0.1–100 mg of the same per kg weight of human being is generally given for the treatment of endothelin-mediated diseases.

In order to illustrate the usefulness of the object compound (I), the pharmacological test datum of a representative compound of the compound (I) is shown in the following.

Test 1
Radioligand binding assay:
(1) Test Compound
   a. Compound A [The compound of Example 65]
(2) Test Method
   (a) Crude receptor membrane preparation:
   Porcine aorta was purchased from Pel-Freez Biologicals (U.S.A.) and stored at −80° C. until use.
   Porcine aorta (50 g) was thawed and dissected free from fatty tissue, minced with scissors and then homogenized with a polytron (Brinkmann PT-20, maximal speed for 3×10 sec) in 100 ml buffer (0.25M sucrose, 10 mM Tris-HCl, 0.1 mM EDTA).
   The homogenate was centrifuged at 10,000 g for 20 minutes at 4° C.
   The supernatant, containing the plasma membrane fraction, was centrifuged at 100,000 g for 60 minutes at 4° C., and then resultant pellets were referred to as crude membrane fractions.
   The pellets were resuspended in 25 ml of binding assay buffer (50 mM Tris-HCl, 100 mM NaCl, 5 mM $MgCl_2$, 1.5 μg/ml phenylmethylsulfonyl fluoride (PMSF), 120 μg/ml bacitracin, 12 μg/ml leupepcin, 6 μg/ml chymostain, 0.1% bovine serum albumin (BSA), pH 7.5).
   The aorta membrane fractions were stored at −80° C. until use.
   (b) $^{125}$I-endothelin-1 binding assay:
   $^{125}$I-Endothelin-1 ($1.67 \times 10^{-11}$M) (Amersham Japan, specific activity: 2000 Ci/m mol) was incubated with 50 μl of aorta membrane preparation in binding assay buffer at room temperature (20°–22° C.) for 60 minutes in a final volume of 250 μl.
   After incubation, the incubation mixture were filtered through Glass-fiber GF/C filter (pretreated with 0.1% polyethylene imine for 3 hours prior to use) using cell harvester (Brandel M-24S). The filters were then washed ten times with a total of 3 ml of the washing buffer (50 mM Tris-HCl, pH 7.5) at 0° C. The filters were counted in a gamma counter (Packard Auto Gamma Model 5650).
(3) Test Results
The results are shown in Table 1.

TABLE 1

| Effect on specific binding of $^{125}$I-endothelin-1 in porcine aorta membrane | |
|---|---|
| Test Compound | $IC_{50}$ (M) |
| A | $5.2 \times 10^{-9}$ |

From the result of the above-mentioned test, it is clear that compound (I) has endothelin antagonistic activity, therefore are useful for the treatment and prevention of endothelin mediated diseases, for example, hypertension, heart disease such as angina pectoris, cardiomyopathy, myocardial infarction or the like, cerebral stroke such as cerebral arterial spasm, cerebral ischemia, cerebrovascular twitch or the like, late phase cerebral spasm after subarachnoid hemorrhage, asthma such as bronchoconstriction or the like, renal failure such as acute renal failure, renal insufficiency caused by pharmaceuticals (e.g. Cisplatin, Cyclosporins, etc.), or the like.

The following examples are given for purpose of illustrating the present invention in detail.

In these examples, there are employed the following abbreviations.

Ac: acetyl
Boc: t-butoxycarbonyl
Bu: butyl
Bzl: benzyl
DMF: dimethylformamide
DMSO: dimethyl sulfoxide
Et: ethyl
HOBT: N-hydroxybenzotriazole
Me: methyl
NMM: N-methylmorpholine
Pac: phenacyl
D-Pya: D-(2-pyridyl)alanine
D-4Pya: D-(4-pyridyl)alanine
TFA: trifluoroacetic acid
TEA: triethylamine
TS or Tos: tosyl
WSCD: 1-ethyl-3-(3-dimethylaminopropyl)carbodiimide
Z: benzyloxycarbonyl
DMAP: dimethylaminopyridine
r.t.: room temperature
Preparation 1-1)

To a mixture of Boc-D-Py-OH (3.00 g), pyrrolidine (0.802 g) and HOBT (1.68 g) in DMF (30 ml) was added WSCD-HCl (2.38 g) under ice-bath cooling. The mixture was stirred overnight at 5° C. The resulting solution was diluted with ethyl acetate (100 ml) and washed with saturated sodium bicarbonate (100 ml×2) and brine (100 ml). The organic layer was dried over magnesium sulfate, and concentrated under reduced pressure. The residue was triturated with isopropyl ether to give Boc-D-Pya-pyrrolidineamide (2.35 g).

mp: 60°–67° C. Rf: 0.31 (MeOH:CHCl$_3$=1:9)
Preparation 1-2)

A solution of Boc-D-Pya-pyrrolidineamide (2.35 g, 7.36 mmol) in TFA (25 ml) was stirred for 1.5 hours at r.t. The solution was concentrated under reduced pressure. The residue was dissolved in chloroform (150 ml) and saturated aqueous sodium bicarbonate (100 ml) was added to the solution. The layers were separated, and the aqueous layer was extracted with chloroform (100 ml×3). The organic layer were combined and washed with brine. The solution was dried over magnesium sulfate and concentrated under reduced pressure to give H-D-Pya-pyrrolidineamide (1.68 g), as a yellow oil.

Rf: 0.06 (MeOH:CHCl$_3$=1:9)
Preparation 1-3)

To a mixture of Boc-D-Trp(Me)-OH (2.72 g), H-D-Pya-pyrrolidineamide (1.88 g) and HOBT (1.27 g) in DMF (30 ml) was added WSCD.HCl (1.80 g) under ice-bath cooling. After being stirred for 2.5 hours at 0° C., the mixture was diluted with ethyl acetate (100 ml), and washed with saturated aqueous sodium bicarbonate (100 ml×2) and brine (100 ml). The organic layer was dried over magnesium sulfate, and concentrated under reduced pressure to give Boc-D-Trp(Me)-D-Pya-pyrrolidineamide (4.25 g) as a light yellow oil.

Rf: 0.52 (MeOH:CHCl$_3$=1:9)

This product was used in a next step without further purification.

Preparation 1-4)

A solution of Boc-D-Trp(Me)-D-Pya-pyrrolidineamide (4.25 g) in TFA (50 ml) was stirred for 1.5 hours at 0° C. TFA was removed in vacuo, and the residue was dissolved in 4N.HCl—AcOEt (50 ml). The mixture was concentrated under reduced pressure. The residue was pulverized with ether (25 ml) to give 2HCl.H-D-Trp(Me)-D-Pya-pyrrolidineamide (4.08 g) as a white powder.

Rf: 0.07 (MeOH:CHCl$_3$=1:9)

Preparation 2-1)

To a solution of benzyl (2R)-2-(carboxymethyl)-4-methylvalerate (500 mg) in dry dichloromethane (10 ml) was added oxalyl chloride (0.2 ml) at 0° C. After the solution was stirred at the same temperature for 1 hour, the solvent was evaporated in vacuo to give benzyl (2R)-2-(chloro-carbonylmethyl)-4-methylvalerate (522 mg) as an oil.

This product was used in a next step without further purification.

Preparation 2-2)

To a mixture of piperidine (0.281 g) and triethylamine (0.304 g) in dichloromethane (10 ml) was added dropwise a solution of benzyl (2R)-2-(chlorocarbonylmethyl)-4-methylvalerate (0.816 g) in dichloromethane (5 ml). The solution was stirred at room temperature for 30 minutes and the solvent was evaporated in vacuo. The residue was dissolved in ethyl acetate (30 ml), and washed with 7% hydrochloric acid, saturated aqueous sodium bicarbonate solution, and saturated aqueous sodium chloride solution successively. The organic layer was dried over magnesium sulfate, and concentrated in vacuo to give benzyl (2R)- 2-(piperidinocarbonylmethyl)-4-methylvalerate (0.931 g) as an oil.

Rf: 0.23 (n-hexane:EtOAc=3:1)

Preparation 2-3)

A solution of benzyl (2R)-2-(piperidinocarbonylmethyl)-4-methylvalerate (0.625 g) in methanol (10 ml) was hydrogenated over 10% palladium on carbon (80 mg) at 3 atmospheric pressure of hydrogen for 1 hour. After removal of the catalyst by filtration, the filtrate was concentrated in vacuo to give (2R)-2-(piperidinocarbonylmethyl)- 4-methylvaleric acid (0.43 g) as an oil.

Rf: 0.38 (MeOH:CHCl$_3$=1:10)

Preparation 3-1)

Boc-D-Pya-dimethylamide (2.26 g) was obtained in substantially the same manner as that of Preparation 1-1).

Rf: 0.74 (CHCl$_3$:MeOH:AcOH=8:1:1)

Preparation 3-2)

H-D-Pya-dimethylamide was obtained in substantially the same manner as that of Preparation 1-2).

Rf: 0.06 (CHCl$_3$:MeOH:AcOH=16:1:1)

Preparation 3-3)

Boc-D-Trp(Me)-D-Pya-dimethylamide was obtained in substantially the same manner as that of Preparation 1-3).

Rf: 0.52 (MeOH:CHCl$_3$=1:9), 0.42 (CHCl$_3$:MeOH:AcOH=16:1:1)

Preparation 3-4)

2HCl.H-D-Trp (Me)-D-Pya-dimethylamide was obtained in substantially the same manner as that of Preparation 11-3).

Rf: 0.07 (MeOH: CHCl$_3$=1:9)

Preparation 4-1)

Boc-D-Pya-ethylamide was obtained in substantially the same manner as that of Preparation 7-1).

mp: 110°–113° C. Rf: 0.36 (CHCl$_3$:MeOH:AcOH= 16:1:1)

Preparation 4-2)

H-D-Pya-ethylamide.2HCl was obtained in substantially the same manner as that of Preparation 11-3).

mp: 193°–194° C. Rf: 0.07 (CHCl$_3$:MeOH=9:1)

Preparation 4-3)

Boc-D-Trp(Me)-D-Pya-ethylamide was obtained in substantially the same manner as that of Preparation 1-3).

mp: 148°–150° C. Rf: 0.60 (CHCl$_3$:MeOH=9:1)

Preparation 4-4)

H-D-Trp(Me)-D-Pya-ethylamide.2HCl was obtained in substantially the same manner as that of Preparation 1-2), except for the presence of anisole as a cation trapping agent.

mp: 105°–110° C. Rf: 0.06 (CHCl$_3$:MeOH=9:1)

Preparation 5-1)

Boc-D-Pya-morpholineamide was obtained in substantially the same manner as that of Preparation 1-1).

Rf: 0.38 (MeOH:CHCl$_3$=1:9)

Preparation 5-2)

H-D-Pya-morpholineamide was obtained in substantially the same manner as that of Preparation 1-2).

Rf: 0.05 (MeOH:CHCl$_3$=1:9)

Preparation 5-3)

Boc-D-Trp(Me)-D-Pya-morpholineamide was obtained in substantially the same manner as that of Preparation 1-3).

mp: 85°–93° C. Rf: 0.51 (CHCl$_3$:MeOH:AcOH=16:1:1)

Preparation 5- 4)

2HCl.H-D-Trp(Me)-D-Pya-morpholineamide was obtained in substantially the same manner as that of Preparation 11-3).

Rf: 0.03 (MeOH: CHCl$_3$=1:9)

Preparation 6-1)

Boc-D-Pya-thiomorpholineamide was obtained in substantially the same manner as that of Preparation 1-1).

mp: 65°–69° C. Rf: 0.29 (CHCl$_3$:MeOH:AcOH=16:1:1)

Preparation 6-2)

H-D-Pya-thiomorpholineamide was obtained in substantially the same manner as that of Preparation 2-2).

Rf: 0.07 (CHCl$_3$MeOH:AcOH=16:1:1)

Preparation 6-3)

Boc-D-Trp(Me)-D-Pya-thiomorpholineamide was obtained in substantially the same manner as that of Preparation 2-3).

mp: 90°–95° C. Rf: 0.31 (CHCl$_3$:MeOH:AcOH=16:1:1)

Preparation 6-4)

2HCl.H-D-Trp(Me)-D-Pya-thiomorpholineamide was obtained in substantially the same manner as that of Preparation 11-3).

Rf: 0.04 (MeOH:CHCl$_3$=1:9)

Preparation 7-1)

To a solution of Boc-D-Pya-OH (0.20 g) in DMF (4 ml) were added piperidine (70 mg), diphenylphosphoryl azide (DPPA) (0.23 g) and triethylamine (76 mg) at room temperature. After being stirred overnight at room temperature, the mixture was diluted with ethyl acetate and washed with water, aqueous sodium bicarbonate and brine, successively. The organic layer was dried over magnesium sulfate and concentrated in vacuo to give Boc-D-Pya-piperidineamide (0.22 g) as an oil.

Rf: 0.59 (CHCl$_3$:MeOH=9:1)

Preparation 7-2 )

H-D-Pya-piperidineamide.2HCl was obtained in substantially the same manner as that of Preparation 11-3).

Rf: 0.30 (CHCl$_3$:MeOH: AcOH=8:2:1)

Preparation 7-3)

Boc-D-Trp(Me)-D-Pya-piperidineamide was obtained in substantially the same manner as that of Preparation 1-3).

Rf: 0.80 (CHCl$_3$:MeOH:AcOH=8:2:1)

Preparation 7-4)

H-D-Trp(Me)-D-Pya-piperidineamide.2HCl was obtained in substantially the same manner as that of Preparation 4-4).

Rf: 0.11 (CHCl]:MeOH=9:1)

Preparation 8-1)

Boc-D-Pya-N,N-dimethylhydrazide was obtained in substantially the same manner as that of Preparation 1-1).

Rf: 0.39 (CHCl$_3$:MeOH:AcOH=16:1:1)
Preparation 8-2)
H-D-Pya-N,N-dimethylhydrazide was obtained in substantially the same manner as that of Preparation 1-2).
Rf: 0.06 (MeOH:CHCl$_3$=1:9)
Preparation 8-3)
Boc-D-Trp(Me)-D-Pya-N,N-dimethylhydrazide was obtained in substantially the same manner as that of Preparation 1-3).
Rf: 0.34 (MeOH: CHCl$_3$=1:9)
Preparation 8-4)
3HCl.H-D-Trp(Me)-D-Pya-N,N-dimethylhydrazide was obtained in substantially the same manner as that of Preparation 11-3).
Rf: 0.05 (MeOH:CHCl$_3$=1:9)
Preparation 9-1)
Boc-D-Pya-(N-morpholino)amide was obtained in substantially the same manner as that of Preparation 1-1).
Rf: 0.33 (CHCl$_3$:MeOH:AcOH=16:1:1)
Preparation 9-2)
H-D-Pya-(N-morpholino)amide was obtained in substantially the same manner as that of Preparation 1-2).
Rf: 0.06 (MeOH:CHCl$_3$=1:9)
Preparation 9-3)
Boc-D-Trp(Me)-D-Pya-(N-morpholino) amide was obtained in substantially the same manner as that of Preparation 1-3).
Rf: 0.43 (MeOH:CHCl$_3$=1:9)
Preparation 9-4)
3HCl.H-D-Trp(Me)-D-Pya-(N-morpholino)amide was obtained in substantially the same manner as that of Preparation 11-3).
Rf: 0.05 (MeOH:CHCl$_3$=1:9)
Preparation 10-1)
Boc-D-Trp(Me)-D-Pya-NH$_2$ was obtained in substantially the same manner as that of Example 74.
mp: 162°–163° C. Rf: 0.47 (CHCl$_3$:MeOH=9:1)
Preparation 10-2)
2HCl-H-D-Trp(Me)-D-Pya-NH$_2$ was obtained in substantially the same manner as that of Preparation 4-4).
Rf: 0.05 (MeOH:CHCl$_3$=1:9)
Preparation 11-1)
(2R)-2-[(tert-Butyloxycarbonyl)methyl]-4-methylvaleric acid was obtained in substantially the same manner as that of Preparation 2-3).
Rf: 0.40 (hexane:AcOEt =2:1)
Preparation 11-2)
[(2R)-2-{(tert-Butyloxycarbonyl)methyl}- 4-methylvaleryl]-D-Trp(Me)-D-Pya-NH$_2$ was obtained in substantially the same manner as that of Preparation 4-3).
mp: 125°–131° C. Rf: 0.47 (CHCl$_3$:MeOH:AcOH= 16:1:1)
Preparation 11-3)
A solution of [(2R)-2-{(tert-butyloxycarbonyl)methyl-4-methylvaleryl]-D-Trp(Me)-D-Pya-NH$_2$ (3.05 g) in 4N.HCl—AcOEt (50 ml) was stirred for 1.5 hours at 0° C. The mixture was evaporated to give [(2R)-2-(carboxymethyl)- 4-methylvaleryl]-D-Trp(Me)-D-Pya-NH$_2$-hydrochloride (2.48 g).
Rf: 0.17 (CHCl$_3$:MeOH:AcOH=8:1:1)
Preparation 12-1)
Benzyl (2R )-2-[N-ethyl-N-(1-ethylpropyl)carbamoyl]-methyl- 4-methylvalerate was obtained in substantially the same manner as that of Preparation 2-2).
Rf: 0.45 (MeOH: CHCl$_3$=1:10)
Preparation 12-2)
(2R)-2-[N-Ethyl-N-(1-ethylpropyl)carbamoyl]methyl-4-methylvaleric acid was obtained in substantially the same manner as that of Preparation 2-3).

Rf: 0.54 (MeOH:CHCl$_3$=1:10)
Preparation 13-1)
Benzyl (2R)-2-[(N-methyl-N-cyclohexylcarbamoyl)methyl]- 4-methylvalerate was obtained in substantially the same manner as that of Preparation 2-2).
Rf: 0.31 (n-hexane:EtOAc=3:1)
Preparation 13-2)
(2R)-2-[(N-Methyl-N-cyclohexylcarbamoyl)methyl-4-methylvaleric acid was obtained in substantially the same manner as that of Preparation 2-3).
Rf: 0.52 (benzene:EtOAc:AcOH=20:20:1)
Preparation 14-1)
Benzyl (2R)-2-[(N-methyl-N-phenylcarbamoyl)methyl]-4-methylvalerate was obtained in substantially the same manner as that of Preparation 2-2).
Rf: 0.32 (n-hexane:EtOAc=3:1)
Preparation 14-2)
(2R)-2-[(N-Methyl-N-phenylcarbamoyl)methyl]-4-methylvaleric acid was obtained in substantially the same manner as that of Preparation 2-3).
Rf: 0.50 (benzene:EtOAc:AcOH=20:20:1)
Preparation 15-1)
Benzyl (2R)-2-[(1,2,3,4-tetrahydroquinolin-1-ylcarbonyl)methyl]- 4-methylvalerate was obtained in substantially the same manner as that of Preparation 2-2).
Rf: 0.85 (MeOH:CHCl$_3$=1:10), 0.38 (hexane:AcOEt =3:1)
Preparation 15-2)
(2R)-2-[1,2,3,4-Tetrahydroquinolin-1-ylcarbonyl)-methyl- 4-methylvaleric acid was obtained in substantially the same manner as that of Preparation 2-3).
Rf: 0.40 (MeOH:CHCl$_3$=1:9)
Preparation 16
To a solution of(2R)-2-[(N-ethyl-N-(1-ethylpropyl)carbamoyl]methyl- 4-methylvaleric acid (421 mg) and pyridine (123 mg) in acetonitrile (6 ml) was added disuccinimidoylcarbonate (600 mg). The suspension was stirred at room temperature overnight to give a clear solution. The solvent was evaporated in vacuo. The residue was dissolved in ethyl acetate (30 ml), washed with 10% aqueous citric acid solution, saturated aqueous sodium bicarbonate solution, and saturated aqueous sodium chloride solution successively, dried over magnesium sulfate, and concentrated in vacuo to give (2R)-2-[N-ethyl-N-(1-ethylpropyl)carbamoyl] methyl-4-methylvaleric acid succinimido ester (572 mg) as an oil.
Rf: 0.62 (MeOH:CHCl$_3$=1:10)
Preparation 17-1)
Benzyl (2R)-2-(N-ethyl-N-isopropylcarbamoyl)methyl-4-methylvalerate was obtained in substantially the same manner as that of Preparation 2-2).
Rf: 0.36 (n-hexane:EtOAc=2:1)
Preparation 17-2)
(2R)-2-(N-Ethyl-N-isopropylcarbamoyl)methyl-4-methylvaleric acid was obtained in substantially the same manner as that of Preparation 2-3).
Rf: 0.51 (MeOH:CHCl$_3$=1:10)
Preparation 17-3)
(2R)-2-(N-Ethyl-N-isopropylcarbamoyl)methyl-4-methylvaleric acid succinimido ester was obtained in substantially the same manner as that of Preparation 16.
Rf: 0.64 (MeOH:CHCl$_3$=1:10)
Preparation 18-1)
Benzyl (2R)-2-[N-propyl-N-(1-ethylpropyl)carbamoyl] methyl- 4-methylvalerate was obtained in substantially the same manner as that of Preparation 2-2).
Rf: 0.54 (n-hexane:EtOAc =2:1)

Preparation 18-2)

(2R)-2-[N-Propyl-N-(1-ethylpropyl)carbamoyl]methyl-4-methylvaleric acid was obtained in substantially the same manner as that of Preparation 2-3).

Rf: 0.58 (benzene:EtOAc:AcOH=20:20:1)

Preparation 18-3)

(2R)-2-[N-Propyl-N-(1-ethylpropyl)carbamoyl]methyl-4-methylvaleric acid succinimido ester was obtained in substantially the same manner as that of Preparation 17-3).

Rf: 0.70 (MeOH:CHCl$_3$=1:10)

Preparation 19-1)

Benzyl (2R)-2-[N-methyl-N-(o-tolyl)carbamoyl]methyl-4-methylvalerate was obtained in substantially the same manner as that of Preparation 2-2).

Rf: 0.47 (n-hexane:EtOAc=2:1)

Preparation 19-2)

(2R)-2-[N-Methyl-N-(o-tolyl)carbamoyl]methyl-4-methylvaleric acid was obtained in substantially the same manner as that of Preparation 2-3).

Rf: 0.49 (benzene:EtOAc:AcOH=20:20:1)

Preparation 19-3)

(2R)-[N-Methyl-N-(o-tolyl)carbamoyl]methyl-4-methylvaleric acid succinimido ester was obtained in substantially the same manner as that of Preparation 17-3).

Rf: 0.56 (MeOH:CHCl$_3$=1:10)

Preparation 20-1)

Benzyl (2R)-2-[(3-azabicyclo[3.2.2]nonan-3-yl)carbonylmethyl]- 4-methylvalerate was obtained in substantially the same manner as that of Preparation 2-2).

Rf: 0.67 (EtOAc:hexane=1:2)

Preparation 20-2)

(2R)-2-[(3-Azabicyclo[3.2.2]nonan-3-yl)carbonylmethyl]- 4-methylvaleric acid was obtained in substantially the same manner as that of Preparation 2-3).

Rf: 0.43 (CHCl$_3$:MeOH=9:1)

Preparation 20-3)

(2R)-2-[(3-Azabicyclo[3.2.2 ]nonan-3-yl)carbonylmethyl]- 4-methylvaleric acid succinimido ester was obtained in substantially the same manner as that of Preparation 17-3).

This product was used in the next step immediately.

Preparation 21-1)

Benzyl (2R)-2-[(N-neopentyl-N-ethylcarbamoyl)methyl]- 4-methylvalerate was obtained in substantially the same manner as that of Preparation 2-2).

Rf: 0.76 (EtOAc:hexane=1:2)

Preparation 21-2)

(2R)-2-[(N-Neopentyl-N-ethylcarbamoyl)methyl]-4-methylvaleric acid was obtained in substantially the same manner as that of Preparation 2-3).

Rf: 0.38 (CHCl$_3$:MeOH=9:1)

Preparation 21-3)

(2R)-2-[(N-Neopentyl-N-ethylcarbamoyl)methyl]-4-methylvaleric acid succinimido ester was obtained in substantially the same manner as that of 17-3).

This product was used in the next step immediately.

Preparation 22-1)

A solution of acetaldehyde (2.53 g) in dioxane (10 ml) was added slowly to a solution of (1-ethylpropyl)amine (5 g) in dioxane (30 ml). The solution was stirred at room temperature for 30 minutes and hydrogenated over 10% palladium on carbon (0.8 g) at 3 atmospheric pressure of hydrogen for 4 hours. After removal of the catalyst by filtration, to the filtrate was added dropwise a solution of di-tert-butyl bicarbonate (12.52 g) in dioxane (20 ml). After being stirred for 30 minutes, the solution was evaporated in vacuo. The residue was dissolved in ethyl acetate, washed with 3% hydrochloric acid, saturated aqueous sodium bicarbonate solution, and saturated aqueous sodium chloride solution successively, dried over magnesium sulfate, and concentrated in vacuo. The residue was purified with silica gel column chromatography (n-hexane:ethyl acetate=10:1 as eluent) to give N-tert-butylcarbonyl-N-ethyl-(1-ethylpropyl)amine (7.05 g). This product was dissolved in 4N hydrogen chloride in ethyl acetate (70 ml). After being stirred at room temperature for 30 minutes, the solvent was evaporated in vacuo. The crystalline residue was washed with ethyl ether to give N-ethyl-N-(1-ethylpropyl)amine hydrochloride (3.66 g).

mp: 142°–143° C.

Preparation 22-2)

To a solution of N-ethyl-N-(1-ethylpropyl)amine hydrochloride (1,517 g) and triethylamine (1.113 g) in dichloromethane (30 ml) was added dropwise a solution of (S)-α-benzyloxycarbonyl-γ-methylbutyl isocyanate (2.472 g) in dichloromethane (10 ml). The solution was stirred at room temperature for 30 minutes and concentrated in vacuo. The residue was dissolved in ethyl acetate (50 ml) and washed with 7% hydrochloric acid, saturated aqueous sodium bicarbonate solution, and saturated aqueous sodium chloride solution successively. The organic layer was dried over magnesium sulfate and concentrated in vacuo. The residue was purified with silica gel column chromatography (EtOAc:n-hexane=1:6 as eluent) to give N-[N-ethyl-N-(1-ethylpropyl)carbamoyl]-L-Leu-OBzl (2.61 g) as an oil.

Rf: 0.40 (EtOAc:n-hexane=1:3)

Preparation 22-3)

N-[N-Ethyl-N-(1-ethylpropyl)carbamoyl]-L-Leu-OH was obtained in substantially the same manner as that of Preparation 2-3).

mp: 56°–57° C. Rf: 0.40 (n-hexane:EtOAc=3:1)

Preparation 23-1)

N-Propyl-N-(1-ethylpropyl)amine hydrochloride was obtained in substantially the same manner as that of Preparation 22-1).

mp: 138° C.

Preparation 23-2)

N-[N-Propyl-N-(1-ethylpropyl)carbamoyl]-L-Leu-OBzl was obtained in substantially the same manner as that of Preparation 22-2).

Rf: 0.48 (n-hexane:EtOAc=2:1)

Preparation 23-3)

N-[N-Propyl-N-(1-ethylpropyl)carbamoyl]-L-Leu-OH was obtained in substantially the same manner as that of Preparation 2-3).

mp: 67°–68° C. Rf: 0.51 (benzene:EtOAc:AcOH= 20:20:1)

Preparation 24-1)

N-(N-Isopropyl-N-ethylcarbamoyl)-L-Leu-OBzl was obtained in substantially the same manner as that of Preparation 22-2).

Rf: 0.43 (EtOAc:hexane=1:2)

Preparation 24-2)

N-(N-Isopropyl-N-ethylcarbmoyl)-L-Leu-OH was obtained in substantially the same manner as that of Preparation 2-3).

mp: 90°–93° C. Rf: 0.37 (CHCl$_3$:MeOH:AcOH=16:1:1)

Preparation 25-1)

N-(3-Azabicyclo[3.2.2]nonan-3-ylcarbonyl)-L-Leu-OBzl was obtained in substantially the same manner as that of Preparation 22-2).

mp: 67°–68° C. Rf: 0.73 (CHCl$_3$:MeOH=9:1)

Preparation 25-2)

N-(3-Azabicyclo[3.2.2]nonan-3-ylcarbonyl)-L-Leu-OH was obtained in substantially the same manner as that of Preparation 2-3).

Rf: 0.30 (CHCl$_3$:MeOH=9:1)

Preparation 26-1)

N-Neopentyl-N-ethylamin.HCl was obtained in substantially the same manner as that of Preparation 22-1).

mp: >250° C.

Preparation 26-2)

N-(N-Neopentyl-N-ethylcarbamoyl)-L-Leu-OBzl was obtained in substantially the same manner as that of Preparation 22-2).

Rf: 0.51

Preparation 26-3)

N-(N-Neopentyl-N-ethylcarbamoyl)-L-Leu-OH was obtained in substantially the same manner as that of Preparation 2-3).

Rf: 0.41 (CHCl$_3$:MeOH:AcOH=16:1:1)

Preparation 27-1)

To a suspension of L-norleucine benzyl ester hydrochloride (505 mg) in toluene (10 ml) was added trichloromethyl chloroformate (0.16 ml), and the mixture was refluxed for 1 hour. Activated carbon (0.1 g) was then added, and the mixture was refluxed for an additional 1 hour. After removal of the activated carbon by filtration, the filtrate was concentrated in vacuo. The crystalline residue was dissolved in ethyl acetate (20 ml), and hexahydro-1H-azepine (283 mg) was added. After stirring for 30 minutes, the solution was washed in turn with 7% hydrochloric acid, saturated aqueous sodium bicarbonate solution, and aqueous sodium chloride solution, dried over magnesium sulfate, and concentrated in vacuo to give N-(hexahydro-1H-azepin-1-ylcarbonyl)-L-Nle-OBzl (632 mg) as an oil.

Rf: 0.30 (n-hexane:EtOAc=2:1)

Preparation 27-2)

N-(Hexahydro-1H-azepin-1-ylcarbonyl)-L-Nle-OH was obtained in substantially the same manner as that of Preparation 2-3).

mp: 107°–108° C. Rf: 0.44 (benzene:EtOAc:AcOH= 20:20:1)

Preparation 28

[(2R)-2-(Octahydroazocin-1-ylcarbonyl)methyl- 4-methylvaleryl]-D-Trp(Me)-D-Pya-OEt Rf: 0.43 (CHCl$_3$:MeOH:AcOH=16:1:1)

Preparation 29

N-Piperidinocarbonyl-L-Leu-D-Trp(Me)-D-Pya-OEt

Rf: 0.44 (MeOH:CHCl$_3$=1:9)

EXAMPLE 1

To a solution of (2R)-2-(piperidinocarbonylmethyl)-4-methylvaleric acid (113 mg) and H-D-Trp(Me)-D-Pya-pyrrolidineamide dihydrochloride (220 mg) in dimethylformamide (3 ml) were added HOBT (61 mg), N-methylmorpholine (46 mg), and WSCD (70 mg) at 0° C. After being stirred at room temperature for 20 hours, the mixture was poured into saturated aqueous ammonium chloride solution, and extracted with ethyl acetate (10 ml×2). The organic layer was washed with saturated aqueous sodium bicarbonate solution and water successively, dried over magnesium sulfate, and concentrated in vacuo. The crystalline residue was washed with a mixture of ethyl acetate and ethyl ether (1:1) to give (2R)-2-(piperidinocarbonylmethyl)- 4-methylvaleryl-D-Trp(Me)-D-Pya-pyrrolidineamide (106 mg).

mp: 100°–102° C. Rf: 0.43 (MeOH:CHCl$_3$=1:10)

EXAMPLE 2

(2R)-2-(N-Methyl-N-cyclohexylcarbamoyl)methyl-4-methylvaleryl-D-Trp(Me)-D-Pya-pyrrolidineamide was obtained in substantially the same manner as that of Example 1.

mp: 119°–121° C. Rf: 0.45 (MeOH:CHCl$_3$=1:10)

EXAMPLE 3

To a solution of (2R)-2-(piperidinocarbonylmethyl)-4-methylvaleryl-D-Trp(Me)-D-Pya-pyrrolidineamide (100 mg) in chloroform (3 ml) was added 4N-hydrogen chloride in ethyl acetate (0.039 ml). The solution was stirred at room temperature for 5 minutes and concentrated in vacuo to give (2R)-2-(piperidinocarbonylmethyl)- 4-methylvaleryl-D-Trp(Me)-D-Pya-pyrrolidineamide hydrochloride (106 mg) as an amorphous powder.

Rf: 0.43 (MeOH:CHCl$_3$=1:10)

The following compounds were obtained in substantially the same manner as that of Example 1.

EXAMPLE 4

[(2R)-2-(Hexahydro-1H-azepin-1-ylcarbonyl)methyl-4-methylvaleryl]-D-Trp(Me)-D-Pya-pyrrolidineamide hydrochloride Rf: 0.33 (CHCl$_3$:MeOH:AcOH=16:1:1)

EXAMPLE 5

[(2R)-2-(Octahydroazocin-1-ylcarbonyl)methyl- 4-methylvaleryl]-D-Trp(Me)-D-Pya-pyrrolidineamide hydrochloride Rf: 0.45 (CHCl$_3$:MeOH:AcOH=16:1:1), 0.41 (MeOH:CHCl$_3$=1:9)

EXAMPLE 6

(2R)-2-(N-Methyl-N-cyclohexylcarbamoyl)methyl-4-methylvaleryl-D-Trp(Me)-D-Pya-pyrrolidineamide hydrochloride was obtained in substantially the same manner as that of Example 3.

Rf: 0.45 (MeOH:CHCl$_3$=1:10)

EXAMPLE 7

Saturated aqueous sodium bicarbonate solution (5 ml) was added slowly to a suspension of H-D-Trp(Me)-D-Pya-pyrrolidineamide dihydrochloride (230 mg) in chloroform (30 ml). The mixture was stirred for 10 minutes and the organic layer was separated. The aqueous layer was extracted with chloroform (10 ml). The combined organic layer was washed with saturated sodium chloride solution (10 ml), dried over magnesium sulfate, and concentrated in vacuo. The residue was dissolved in DMF (3 ml). To this solution was added (2R)-2-[N-ethyl-N-(1-ethylpropyl)carbamoyl]methyl-4-methylvaleric acid succinimido ester (186 mg). After being stirred at room temperature overnight, the solution was poured into saturated aqueous ammonium chloride solution, and extracted with ethyl acetate (20 ml×2). The organic layer was washed with saturated aqueous sodium bicarbonate solution and saturated aqueous sodium chloride solution successively, dried over magnesium sulfate, and concentrated in vacuo. The crystalline residue was washed with ethyl ether to give (2R)-2-[N-ethyl-N-(1-ethylpropyl)carbamoyl]methyl- 4-methylvaleryl-D-Trp(Me)-D-Pya-pyrrolidineamide (116 mg).

mp: 96°–98° C. Rf: 0.53 (MeOH:CHCl$_3$=1:10)

EXAMPLE 8

(2R)-2-[N-Ethyl-N-(1-ethylpropyl)carbamoyl]methyl-4-methylvaleryl-D-Trp(Me)-D-Pya-pyrrolidineamide hydrochloride was obtained in substantially the same manner as that of Example 3.

Rf: 0.53 (MeOH:CHCl$_3$=1:10)

The following compounds were obtained in substantially the same manner as that of Example 7.

EXAMPLE 9

(2R)-2-(N-Ethyl-N-isopropylcarbamoyl)methyl- 4-methylvaleryl-D-Trp(Me)-D-Pya-pyrrolidineamide mp: 103°–110° C. Rf: 0.43 (MeOH:CHCl$_3$=1:10)

EXAMPLE 10

(2R)-2-[N-Propyl-N-(1-ethylpropyl)carbamoyl]methyl-4-methylvaleryl-D-Trp(Me)-D-Pya-pyrrolidineamide mp: 93°–96° C. Rf: 0.43 (MeOH:CHCl$_3$=1:10)

EXAMPLE 11

(2R)-2-(3-Azabicyclo[3.2.2]nonan-3-ylcarbonylmethyl) 4-methylvaleryl-D-Trp(Me)-D-Pya-pyrrolidineamide mp: 97°–103° C. Rf: 0.56 (CHCl$_3$:MeOH=9:1)

EXAMPLE 12

(2R)-2-(N-Neopentyl-N-ethylcarbamoylmethyl)- 4-methylvaleryl-D-Trp(Me)-D-Pya-pyrrolidineamide mp: 106°–122° C. Rf: 0.51 (CHCl$_3$:MeOH=9:1)

The following compounds were obtained in substantially the same manner as that of Example 1.

EXAMPLE 13

N-(Piperidinocarbonyl)-L-Leu-D-Trp(Me)-D-Pya-pyrrolidineamide

Rf: 0.31 (MeOH:CHCl$_3$=1:9)

EXAMPLE 14

N-Octahydroazocin-1-ylcarbonyl-L-Leu-D-Trp(Me)-D-Pya-pyrrolidineamide

Rf: 0.32 (MeOH:CHCl$_3$=1:9)

EXAMPLE 15

N-(Isopropyl-N-ethylcarbamoyl)-L-Leu-D-Trp(Me)-D-Pya-pyrrolidineamide

Rf: 0.43 (MeOH:CHCl$_3$=1:9)

EXAMPLE 16

N-[N-Propyl-N-(1-ethylpropyl)carbamoyl]-L-Leu-D-Trp(Me)-D-Pya-pyrrolidineamide

Rf: 0.52 (MeOH:CHCl$_3$=1:10)

EXAMPLE 17

N-[N-Ethyl-N-(1-ethylpropyl)carbamoyl]-L-Leu-D-Trp(Me)-D-Pya-pyrrolidineamide

Rf: 0.32 (MeOH:CHCl$_3$=1:10)

EXAMPLE 18

N-(3-Azabicyclo[3.2.2]nonan-3-yl)carbonyl-L-Leu-D-TrP(Me)-D-Pya-pyrrolidineamide Rf: 0.39 (MeOH:CHCl$_3$=1:9)

EXAMPLE 19

N-(N-Neopentyl-N-ethylcarbamoyl)-L-Leu-D-Trp(Me)-D-Pya-pyrrolidineamide

Rf: 0.57 (CHCl$_3$:MeOH=9:1)

EXAMPLE 20

[(2R)-2-(1-Piperidinocarbonyl)methyl- 4-methylvaleryl]-D-Trp(Me)-D-Pya-dimethylamide hydrochloride Rf: 0.33 (MeOH:CHCl$_3$=1:9)

EXAMPLE 21

[(2R)-2-(Hexahydro-1H-azepin-1-ylcarbonyl)methyl-4-methylvaleryl]-D-Trp(Me)-D-Pya-dimethylamide hydrochloride Rf: 0.33 (CHCl$_3$:MeOH:AcOH=16:1:1)

EXAMPLE 22

[(2R)-2-(Octahydroazocin-1-ylcarbonyl)methyl- 4-methylvaleryl]-D-Trp(Me)-D-Pya-dimethylamide hydrochloride Rf: 0.45 (MeOH:CHCl$_3$=1:9)

EXAMPLE 23

(2R)-2-(N-Methyl-N-phenylcarbamoyl)methyl- 4-methylvaleryl-D-Trp(Me)-D-Pya-dimethylamide hydrochloride Rf: 0.51 (MeOH:CHCl$_3$=1:10)

EXAMPLE 24

(2R)-2-(N-Methyl-N-cyclohexylcarbamoyl)methyl-4-methylvaleryl-D-Trp(Me)-D-Pya-dimethylamide Rf: 0.53 (MeOH:CHCl$_3$=1:10)

EXAMPLE 25

(2R)-2-(N-Methyl-N-cyclohexylcarbamoyl)methyl-4-methylvaleryl-D-Trp(Me)-D-Pya-dimethylamide hydrochloride was obtained in substantially the same manner as that of Example 3.

Rf: 0.53 (MeOH:CHCl$_3$=1:10)

The following compounds were obtained in substantially the same manner as that of Example 7.

EXAMPLE 26

(2R)-2-(3-Azabicyclo[3.2.2]nonan-3-ylcarbonylmethyl)-4-methylvaleryl-D-Trp(Me)-D-Pya-dimethylamide mp: 103°–105° C. Rf: 0.49 (CHCl$_3$:MeOH=9:1)

EXAMPLE 27

(2R)-2-[(N-Neopentyl-N-ethylcarbamoyl)methyl]- 4-methylvaleryl-D-Trp(Me)-D-Pya-dimethylamide mp: 94°–101° C. Rf: 0.51 (CHCl$_3$MeOH=9:1)

EXAMPLE 28

(2R)-2-(N-Ethyl-N-isopropylcarbamoyl)methyl- 4-methylvaleryl-D-Trp(Me)-D-Pya-dimethylamide mp: 96°–99° C. Rf: 0.53 (MeOH:CHCl$_3$=1:10)

EXAMPLE 29

(2R)-2-[N-Propyl-N-(1-ethylpropyl)carbamoyl]methyl-4-methylvaleryl-D-Trp(Me)-D-Pya-dimethylamide mp: 97°–100° C. Rf: 0.50 (MeOH:CHCl$_3$=1:10)

EXAMPLE 30

(2R)-2-[N-Methyl-N-(o-tolyl)carbamoyl]methyl- 4-methylvaleryl-D-Trp(Me)-D-Pya-dimethylamide hydrochloride was obtained in substantially the same manner as that of Example 3.

Rf: 0.53 (MeOH:CHCl$_3$=1:10)

EXAMPLE 31

(2R)-2-[N-Methyl-N-(o-tolyl)carbamoyl]methyl- 4-methylvaleryl-D-Trp(Me)-D-Pya-dimethylamide was obtained in substantially the same manner as that of Example 7.

mp: 105°–107° C. Rf: 0.53 (MeOH:CHCl$_3$=1:10)

The following compounds were obtained in substantially the same manner as that of Example 1.

EXAMPLE 32

N-Piperidinocarbonyl-L-Leu-D-Trp(Me)-D-Pya-dimethylamide

Rf: 0.43 (MeOH:CHCl$_3$=1:9)

EXAMPLE 33

N-(Octahydroazocin-1-ylcarbonyl)-L-Leu-D-Trp(Me)-D-Pya-dimethylamide

Rf: 0.32 (MeOH:CHCl$_3$=1:9)

EXAMPLE 34

N-(N-Isopropyl-N-ethylcarbamoyl)-L-Leu-D-Trp(Me)-D-Pya-dimethylamide

Rf: 0.43 (MeOH:CHCl$_3$=1:9)

EXAMPLE 35

N-[N-Ethyl-N-(1-ethylpropyl)carbamoyl]-L-Leu-D-Trp(Me)-D-Pya-dimethylamide

Rf: 0.39 (MeOH:CHCl$_3$=1:10)

EXAMPLE 36

N-(3-Azabicyclo[3.2.2]nonan-3-yl)carbonyl-L-Leu-D-Trp(Me)-D-Pya-dimethylamide

Rf: 0.30 (MeOH:CHCl$_3$=1:9)

EXAMPLE 37

N-[N-Propyl-N-(1-ethylpropyl)carbamoyl]-L-Leu-D-Trp(Me)-D-Pya-dimethylamide

Rf: 0.55 (MeOH:CHCl$_3$=1:10)

EXAMPLE 38

N-(N-Neopentyl-N-ethylcarbamoyl)-L-Leu-D-Trp(Me)-D-Pya-dimethylamide

Rf: 0.51 (CHCl$_3$:MeOH=9:1)

EXAMPLE 39

N-Piperidinocarbonyl-L-Leu-D-Trp(Me)-D-Pya-ethylamide

Rf: 0.29 (MeOH:CHCl$_3$=1:9)

EXAMPLE 40

N-Octahydroazocin-1-ylcarbonyl-L-Leu-D-Trp(Me)-D-Pya-ethylamide

Rf: 0.36 (MeOH:CHCl$_3$=1:9)

EXAMPLE 41

(2R)-2-(Piperidinocarbonylmethyl)-4-methylvaleryl-D-Trp(Me)-D-Pya-morpholineamide mp: 107°–110° C. Rf: 0.50 (MeOH:CHCl$_3$=1:10)

EXAMPLE 42

(2R)-2-(Piperidinocarbonylmethyl)-4-methylvaleryl-D-Trp(Me)-D-Pya-morpholineamide hydrochloride was obtained in substantially the same manner as that of Example 3.

Rf: 0.50 (MeOH:CHCl$_3$=1:10)

The following compounds were obtained in substantially the same manner as that of Example 1.

EXAMPLE 43

[(2R)-2-(Hexahydro-1H-azepin-1-yl)carbonylmethyl-4-methylvaleryl]-D-Trp(Me)-D-Pya-morpholineamide hydrochloride Rf: 0.33 (CHCl$_3$:MeOH:AcOH=16:1:1)

EXAMPLE 44

[(2R)-2-(Octahydroazocin-1-ylcarbonyl)methyl- 4-methylvaleryl]-D-Trp(Me)-D-Pya-morpholineamide hydrochloride Rf: 0.40 (CHCl$_3$:MeOH:AcOH=16:1:1)

EXAMPLE 45

(2R)-2-(N-Methyl-N-cyclohexylcarbamoyl)methyl-4-methylvaleryl-D-Trp(Me)-D-Pya-morpholineamide hydrochloride Rf: 0.33 (MeOH:CHCl$_3$=1:10)

EXAMPLE 46

N-Piperidinocarbonyl-L-Leu-D-Trp(Me)-D-Pya-morpholineamide

Rf: 0.44 (MeOH:CHCl$_3$=1:9)

EXAMPLE 47

N-[N-Ethyl-N-(1-ethylpropyl)carbamoyl]-L-Leu-D-TrP(Me)-D-Pya-morpholineamide

Rf: 0.42 (MeOH:CHCl$_3$=1:10)

EXAMPLE 48

N-(Octahydroazocin-1-ylcarbonyl)-L-Leu-D-Trp(Me)-D-Pya-morpholineamide

Rf: 0.37 (MeOH:CHCl$_3$=1:9)

EXAMPLE 49

[(2R)-2-(Hexahydro-1H-azepin-1-ylcarbonyl)methyl-4-methylvaleryl]-D-Trp(Me)-D-Pya-thiomorpholineamide hydrochloride Rf: 0.34 (CHCl$_3$:MeOH:AcOH=16:1:1)

EXAMPLE 50

(2R)-2-(Hexahydro-1H-azepin-1-ylcarbonyl)methyl-4-methylvaleryl-D-Trp(Me)-D-Pya-piperidineamide hydrochloride mp: 122°–127° C. Rf: 0.60 (CHCl$_3$:MeOH=9:1)

EXAMPLE 51

[(2R)-2-(Hexahydro-1H-azepin-1-ylcarbonyl)methyl-4-methylvaleryl]-D-Trp(Me)-D-Pya-N',N'-dimethylhydrazide dihydrochloride Rf: 0.36 (CHCl$_3$:MeOH:AcOH=16:1:1)

EXAMPLE 52

[(2R)-2-(Hexahydro-1H-azepin-1-ylcarbonyl)methyl-4-methylvaleryl]-D-Trp(Me)-D-Pya-(N-morpholino)amide hydrochloride Rf: 0.33 (CHCl$_3$:MeOH:AcOH=16:1:1)

EXAMPLE 53

(2R)-2-(Hexahydro-1H-azepin-1-ylcarbonyl)methyl-4-methylvaleryl-D-Trp(Me)-D-Pya-[N-(4-methylpiperazin-1-yl)amide]trihydrochloride was obtained from (2R)-2-(hexahydro-1H-azepin-1-ylcarbonyl)methylvaleryl-D-Trp(Me)-D-Pya-OH in substantially the same manner as that of Preparation 1-1) in the presence of HOBT.

Rf: 0.46 (CHCl$_3$:MeOH=9:1)

The following compounds were obtained from corresponding starting compounds in substantially the same manner as that of Example 53.

EXAMPLE 54

(2R)-2-(Hexahydro-1H-azepin-1-ylcarbonyl)methyl-4-methylvaleryl-D-Trp(Me)-D-Pya-ethylamide hydrochloride Rf: 0.53 (CHCl$_3$:MeOH=9:1)

EXAMPLE 55

(2R)-2-(Hexahydro-1H-azepin-1-ylcarbonyl)methyl-4-methylvaleryl-D-Trp(Me)-D-Pya-2-methoxyethylamide hydrochloride Rf: 0.52 (CHCl$_3$:MeOH=9:1)

EXAMPLE 56

(2R)-2-(Hexahydro-1H-azepin-1-ylcarbonyl)methyl-4-methylvaleryl-D-Trp(Me)-D-Pya-(2-morpholinoethyl)amide dihydrochloride Rf: 0.51 (CHCl$_3$:MeOH=9:1)

EXAMPLE 57

(2R)-2-(Hexahydro-1H-azepin-1-ylcarbonyl)methyl-4-methylvaleryl-D-Trp(Me)-D-Pya-3-(2-oxopyrrolidin-1-yl)propylamide hydrochloride Rf: 0.47 (CHCl$_3$:MeOH=9:1)

EXAMPLE 58

(2R)-2-(Hexahydro-1H-azepin-1-ylcarbonyl)methyl-4-methylvaleryl-D-Trp(Me)-D-Pya-2-(1-piperidyl)ethylamide dihydrochloride Rf: 0.26 (CHCl$_3$:MeOH=9:1)

EXAMPLE 59

(2R)-2-(Hexahydro-1H-azepin-1-ylcarbonyl)methyl-4-methylvaleryl-D-Trp(Me)-D-Pya-2-(2-pyridylethyl)amide dihydrochloride mp: 75°–90° C. Rf: 0.34 (CHCl$_3$:MeOH=9:1)

The following compounds were obtained in substantially the same manner as that of Example 7.

EXAMPLE 60

(2R)-2-(3-Azabicyclo[3.2.2]nonan-3-ylcarbonylmethyl)-4-methylvaleryl-D-Trp(Me)-D-Pya-NH$_2$ Rf: 0.44 (CHCl$_3$:MeOH=9:1)

EXAMPLE 61

(2R)-2-(N-Neopentyl-N-ethylcarbamoylmethyl)-4-methylvaleryl-D-Trp(Me)-D-Pya-NH$_2$ Rf: 0.46 (CHCl$_3$:MeOH=9:1)

EXAMPLE 62

(2R)-2-(N-Ethyl-N-isopropylcarbamoyl)methyl-4-methylvaleryl-D-Trp(Me)-D-Pya-NH$_2$ Rf: 0.37 (MeOH:CHCl$_3$=1:10)

EXAMPLE 63

(2R)-2-[N-Propyl-N-(1-ethylpropyl)carbamoyl]methyl-4-methylvaleryl-D-Trp(Me)-D-Pya-NH$_2$ Rf: 0.39 (MeOH:CHCl$_3$=1:10)

EXAMPLE 64

N-Piperidinocarbonyl-L-Leu-D-Trp(Me)-D-Pya-NH$_2$ was obtained in substantially the same manner as that of Example 1.

Rf: 0.18 (MeOH:CHCl$_3$=1:9)

EXAMPLE 65

[(2R)-2-(Piperidinocarbonyl)methyl-4-methylvaleryl]-D-TrP(Me)-D-Pya-NH$_2$ hydrochloride was obtained from (2R)-2-(carboxymethyl)-4-methylvaleryl]-D-Trp(Me)-D-Pya-NH$_2$ hydrochloride in substantially the same manner as that of Example 1.

Rf: 0.53 (CHCl$_3$:MeOH:AcOH=8:1:1)

The following compounds were obtained in substantially the same manner as that of Example 65.

EXAMPLE 66

[(2R)-2-(N,N-Dipropylcarbamoyl)methyl-4-methylvaleryl]-D-TrP(Me)-D-Pya-NH$_2$ hydrochloride Rf: 0.69 (CHCl$_3$:MeOH:AcOH=8:1:1)

EXAMPLE 67

[(2R)-2-(N-Butyl-N-methylcarbamoyl)methyl-4-methylvaleryl]-D-TrP(Me)-D-Pya-NH$_2$ hydrochloride Rf: 0.61 (CHCl$_3$:MeOH:AcOH=8:1:1)

EXAMPLE 68

[(2R)-2-(Octahydroazocin-1-ylcarbonyl)methyl-4-methylvaleryl]-D-TrP(Me)-D-Pya-NH$_2$ hydrochloride mp: 119°–123° C.

Rf: 0.70 (CHCl$_3$:MeOH:AcOH=8:1:1)

EXAMPLE 69

(2R)-2-[N-Ethyl-N-(1-ethylpropyl)carbamoyl]methyl-4-methylvaleryl-D-Trp(Me)-D-Pya-NH$_2$ hydrochloride Rf: 0.40 (MeOH:CHCl$_3$=1:10)

EXAMPLE 70

(2R)-2-(N-Methyl-N-cyclohexylcarbamoyl)methyl-4-methylvaleryl-D-Trp(Me)-D-Pya-NH$_2$ hydrochloride Rf: 0.53 (MeOH:CHCl$_3$=1:10)

EXAMPLE 71

(2R)-2-(4-Methylpiperidinocarbonyl)methyl- 4-methylvaleryl-D-Trp(Me)-D-Pya-NH$_2$ hydrochloride Rf: 0.53 (MeOH:CHCl$_3$=1:10)

EXAMPLE 72

(2R)-2-(Indolin-1-ylcarbonyl)methyl- 4-methylvaleryl-D-Trp(Me)-D-Pya-NH$_2$ hydrochloride Rf: 0.49 (MeOH:CHCl$_3$=1:10)

EXAMPLE 73

(2R)-2-(N-Ethyl-N-butylcarbamoyl)methyl- 4-methylvaleryl-D-Trp(Me)-D-Pya-NH$_2$ hydrochloride Rf: 0.43 (MeOH:CHCl$_3$=1:10)

EXAMPLE 74

N-[N-Ethyl-N-(1-ethylpropyl)carbamoyl]-L-Leu-D-Trp(Me)-D-Pya-OEt (100 mg) was dissolved in 5.3N ammonia in methanol (5 ml). The solution was allowed to stand at room temperature for 2 days and concentrated in vacuo to give N-[N-ethyl-N-(1-ethylpropyl)carbamoyl]-L-Leu-D-Trp(Me)-D-Pya-NH$_2$ (95 mg) as an amorphous powder.

Rf: 0.41 (MeOH:CHCl$_3$=1:10)

The following compounds were obtained in substantially the same manner as that of Example 74.

EXAMPLE 75

N-[N-Propyl-N-(1-ethylpropyl)carbamoyl]-L-Leu-D-Trp(Me)-D-Pya-NH$_2$

Rf: 0.38 (MeOH:CHCl$_3$=1:10)

EXAMPLE 76

N-(Octahydroazocin-1-ylcarbonyl)-L-Leu-D-Trp(Me)-D-Pya-NH$_2$ mp: 105°–110° C. Rf: 0.45 (CHCl$_3$:MeOH=9:1)

EXAMPLE 77

N-(N-Neopentyl-N-ethylcarbamoyl)-L-Leu-D-Trp(Me)-D-Pya-NH$_2$ mp: 95°–100° C. Rf: 0.44 (CHCl$_3$:MeOH=9:1)

EXAMPLE 78

N-[(1S)-{1-(Dimethylcarbamoyl)-2,2-dimethylpropyl}carbamoyl]-L-Leu-D-Trp(Me)-D-Pya-NH$_2$ mp: 226°–227° C. Rf: 0.23 (MeOH:CHCl$_3$=1:10)

EXAMPLE 79

N-Piperidinocarbonyl-L-Leu-D-Trp(Me)-D-Pya-methylamide

Rf: 0.41 (MeOH:CHCl$_3$=1:9)

EXAMPLE 80

N-(Octahydroazocin-1-yl)-L-Leu-D-Trp(Me)-D-Pya-methylamide mp: 169°–172° C. Rf: 0.56 (CHCl$_3$:MeOH=9:1)

EXAMPLE 81

N-(N-Neopentyl-N-ethylcarbamoyl)-L-Leu-D-Trp(Me)-D-Pya-methylamide

Rf: 0.55 (CHCl$_3$:MeOH=9:1)

EXAMPLE 82

(2R)-2-(N-Methyl-N-phenylcarbamoyl)methyl- 4-methylvaleryl-D-TrP(Me)-D-Pya-NH$_2$ hydrochloride was obtained in substantially the same manner as that of Example 3.

Rf: 0.41 (MeOH:CHCl$_3$=1:10)

EXAMPLE 83

[(2R)-2-(1,2,3,4-Tetrahydroquinolin-1-ylcarbonyl)methyl- 4-methylvaleryl]-D-TrP(Me)-D-Pya-NH$_2$ hydrochloride was obtained in substantially the same manner as that of Example 74.

Rf: 0.26 (MeOH:CHCl$_3$=1:9)

EXAMPLE 84

(2R)-2-(N-Methyl-N-cyclohexylcarbamoyl)methyl-4-methylvaleryl-D-Trp(Me)-D-Pya-methylamide hydrochloride was obtained in substantially the same manner as that of Example 3.

Rf: 0.38 (MeOH:CHCl$_3$=1:10)

The following compounds were obtained in substantially the same manner as that of Example 74.

EXAMPLE 85

[(2R)-2-(Piperidinocarbonyl)methyl- 4-methylvaleryl]-D-Trp(Me)-D-Pya-methylamino hydrochloride Rf: 0.40 (MeOH:CHCl$_3$=1:9)

EXAMPLE 86

[(2R)-2-(Octahydroazocin-1-ylcarbonyl)methyl- 4-methylvaleryl]-D-Trp(Me)-D-Pya-methylamide hydrochloride Rf: 0.38 (MeOH:CHCl$_3$=1:9)

EXAMPLE 87

(2R)-2-(N-Methyl-N-phenylcarbamoyl)methyl- 4-methylvaleryl-D-Trp(Me)-D-Pya-NH$_2$ Rf: 0.41 (MeOH:CHCl$_3$=1:10)

EXAMPLE 88

(2R)-2-(N-Methyl-N-cyclohexylcarbamoyl)methyl-4-methylvaleryl-D-Trp(Me)-D-Pya-methylamide Rf: 0.38 (MeOH:CHCl$_3$=1:10)

EXAMPLE 89

1N Aqueous sodium hydroxide solution (0.3 ml) was added to a solution of (2R)-2-[N-ethyl-N-(1-ethylpropyl)carbamoyl]methyl- 4-methylvaleryl-D-Trp(Me)-D-Pya-OEt (72 mg) in ethanol (1 ml). After being stirred at room temperature for 10 minutes, 1N hydrochloric acid (0.3 ml) was added to the solution and the solvent was evaporated in vacuo. The residue was dissolved in ethyl acetate (20 ml), washed with saturated aqueous sodium chloride solution, dried over magnesium sulfate, and evaporated in vacuo. The residue (64 mg) was dissolved in sodium hydroxide solution (0.103 mmol in 10 ml water) and lyophilized to give (2R)-2-[N-ethyl-N-(1-ethylpropyl)carbamoyl]methyl-4-methylvaleryl-D-Trp(Me)-D-Pya-ONa (66 mg) as a white powder.

Rf: 0.58 (CHCl$_3$:MeOH:AcOH=8:1:1)

The following compounds were obtained in substantially the same manner as that of Example 89.

EXAMPLE 90

N-[N-Ethyl-N-(1-ethylpropyl)carbamoyl]-L-Leu-D-Trp(Me)-D-Pya-ONa

Rf: 0.30 (CHCl$_3$:MeOH:AcOH=8:1:1)

EXAMPLE 91

N-(Hexahydro-1H-azepin-1-ylcarbonyl)-L-Nle-D-Trp(Me)-D-Pya-ONa

Rf: 0.66 (CHCl$_3$:MeOH:AcOH=8:2:1)

EXAMPLE 92

N-[N-Propyl-N-(1-ethylpropyl)carbamoyl]-L-Leu-D-Trp(Me)-D-Pya-ONa

Rf: 0.32 (CHCl$_3$:MeOH:AcOH=8:1:1)

EXAMPLE 93

N-(N-Ethyl-N-isopropylcarbamoyl)-L-Leu-D-Trp(Me)-D-Pya-ONa

Rf: 0.26 (CHCl$_3$:MeOH:AcOH=8:1:1)

The following compounds were obtained in substantially the same manner as that of Example 1.

EXAMPLE 94

[(2R)-2-(1,2,3,4-Tetrahydroquinolin-1-ylcarbonyl)-methyl- 4-methylvaleryl]-D-Trp(Me)-D-Pya-OEt Rf: 0.41 (CHCl$_3$:MeOH:AcOH=16:1:1), 0.72 (MeOH:CHCl$_3$=1:9)

EXAMPLE 95

[(2R)-2-(Piperidinocarbonyl)methyl-4-methylvaleryl]-D-Trp(Me)-D-Pya-OEt

Rf: 0.43 (CHCl$_3$:MeOH:AcOH=16:1:1)

EXAMPLE 96

(2R)-2-[N-Ethyl-N-(1-ethylpropyl)carbamoyl]methyl-4-methylvaleryl-D-Trp(Me)-D-Pya-OEt mp: 61°–63° C. Rf: 0.33 (MeOH:CHCl$_3$=1:20)

EXAMPLE 97

(2R)-2-(N-Methyl-N-phenylcarbamoylmethyl 4-methylvaleryl-D-Trp(Me)-D-Pya-OEt

Rf: 0.38 (MeOH:CHCl$_3$=1:20)

EXAMPLE 98

N-[N-Propyl-N-(1-ethylpropyl)carbamoyl]-L-Leu-D-Trp(Me)-D-Pya-OEt

Rf: 0.46 (EtOAc only)

EXAMPLE 99

N-[N-Ethyl-N-(1-ethylpropyl)carbamoyl]-L-Leu-D-Trp(Me)-D-Pya-OEt

Rf: 0.44 (EtOAc only)

EXAMPLE 100

N-(N-Isopropyl-N-ethylcarbamoyl)-L-Leu-D-Trp(Me)-D-Pya-OEt

Rf: 0.63 (CHCl$_3$:MeOH=9:1)

EXAMPLE 101

N-(3-Azabicyclo[3.2.2]nonan-3-ylcarbonyl)-L-Leu-D-Trp(Me)-D-Pya-OEt

Rf: 0.66 (CHCl$_3$:MeOH=9:1)

EXAMPLE 102

N-(N-Neopentyl-N-ethylcarbamoyl)-L-Leu-D-Trp(Me)-D-Pya-OEt

Rf: 0.62 (CHCl$_3$:MeOH=9:1)

EXAMPLE 103

N-(Hexahydro-1H-azepin-1-ylcarbonyl-L-Nle-D-Trp(Me)-D-Pya-OEt

Rf: 0.52 (MeOH:CHCl$_3$=1:10)

EXAMPLE 104

To a solution of (2R)-2-(N-methyl-N-cyclohexylcarbamoyl)methyl-4-methylvaleric acid (174 mg) in dichloromethane (5 ml) were added oxalyl chloride (0.067 ml) and trace of dimethylformamide. After being stirred at room temperature for 1 hour, a solution of H-D-Trp(Me)-D-Pya-OEt dihydrochloride (300 mg) and N-methylmorpholine (197 mg) in dichloromethane (3 ml) was added to the solution. After being stirred at room temperature for 30 minutes, the solvent was evaporated in vacuo. The residue was dissolved in ethyl acetate (20 ml), washed with saturated aqueous ammonium chloride solution, saturated aqueous sodium bicarbonate solution, and saturated aqueous sodium chloride solution successively, dried over magnesium sulfate, and evaporated in vacuo. The residue was purified with silica gel column chromatography (MeOH:CHCl$_3$=1:100 as an eluent) to give (2R)-2-(N-methyl-N-cyclohexylcarbamoyl)methyl- 4-methylvaleryl-D-Trp(Me)-D-Pya-OEt (82 mg).

EXAMPLE 105

Rf: 0.47 (MeOH:CHCl$_3$=1:20)

(2R)-2-(N-Ethyl-N-isopropylcarbamoyl)methyl- 4-methylvaleryl-D-Trp(Me)-D-Pya-OEt was obtained in substantially the same manner as that of Example 7.

Rf: 0.30 (CHCl$_3$:MeOH=20:1)

EXAMPLE 106

(2R)-2-(Piperidinocarbonyl)methyl-4-methylvaleryl-D-Trp(Me)-D-Pya-ONa was obtained in substantially the same manner as that of Example 89.

Rf: 0.40 (CHCl$_3$:MeOH:AcOH=8:1:1)

EXAMPLE 107

(2R)-2-[N-Propyl-N-(1-ethylpropyl)carbamoyl]methyl-4-methylvaleryl-D-Trp(Me)-D-Pya-ONa was obtained in substantially the same manner as that of Example 89.

Rf: 0.58 (CHCl$_3$:MeOH:AcOH=8:1:1)

EXAMPLE 108

(2R)-2-[N-Propyl-N-(1-ethylpropyl)carbamoyl]methyl-4-methylvaleryl-D-Trp(Me)-D-Pya-OEt was obtained in substantially the same manner as that of Example 7.

Rf: 0.36 (CHCl$_3$:MeOH=20:1)

EXAMPLE 109

(2R)-2-(3-Azabicyclo[3.2.2]nonan-3-ylcarbonyl)methyl-4-methylvaleryl-D-Trp(Me)-D-Pya-ONa was obtained in substantially the same manner as that of Example 89.

Rf: 0.58 (CHCl$_3$:MeOH:AcOH=8:1:1)

EXAMPLE 110

(2R)-2-(3-Azabicyclo[3.2.2]nonan-3-ylcarbonyl)methyl-4-methylvaleryl-D-Trp(Me)-D-Pya-OEt was obtained in substantially the same manner as that of Example 7.

Rf: 0.38 (CHCl$_3$:MeOH=20:1)

EXAMPLE 111

N-(3-Azabicyclo[3.2.2]nonan-3-ylcarbonyl)-L-Leu-D-Trp(Me)-D-Pya-methylamide was obtained in substantially the same manner as that of Example 74.

mp: 144°–156° C. Rf: 0.62 (CHCl$_3$:MeOH=9:1)

EXAMPLE 112

N-(3-Azabicyclo[3.2.2]nonan-3-ylcarbonyl)-L-Leu-D-Trp(Me)-D-Pya-NH$_2$ was obtained in substantially the same manner as that of Example 74.

mp: 125°–130° C. Rf: 0.54 (CHCl$_3$:MeOH=9:1)

EXAMPLE 113

N-(3-Azabicyclo[3.2.2]nonan-3-ylcarbonyl)-L-Leu-D-Trp(Me)-D-Pya-ONa was obtained in substantially the same manner as that of Example 89.

Rf: 0.35 (CHCl$_3$:MeOH:AcOH=8:1:1)

EXAMPLE 114

(2R)-2-(N-Ethyl-N-isopropylcarbamoyl)methyl-4-methylvaleryl-D-Trp(Me)-D-Pya-ONa was obtained in substantially the same manner as that of Example 89.

Rf: 0.50 (CHCl$_3$:MeOH:AcOH 8:1:1)

The following compounds were obatined in substantially the same manner as tht of Example 65.

EXAMPLE 115

(2R)-2-(piperidinocarbonylmethyl)- 4-methylvaleryl-D-Trp(Me)-D-Pya-pyrrolidineamide Rf: 0.43 (MeOH:CHCl$_3$=1:10)

EXAMPLE 116

(2R)-2-(piperidinocarbonylmethyl)-4-methylvaleryl-D-Trp(Me)-D-Pya-pyrrolidineamide hydrochloride Rf: 0.43 (MeOH:CHCl$_3$=1:10)

The following compounds were obatined in substantially the same manner as tht of Example 74.

EXAMPLE 117

(2R)-2-(piperidinocarbonylmethyl)-4-methylvaleryl-D-Trp(Me)-D-Pya-pyrrolidineamide Rf: 0.43 (MeOH:CHCl$_3$=1:10)

EXAMPLE 118

(2R)-2-(piperidinocarbonylmethyl)-4-methylvaleryl-D-Trp(Me)-D-Pya-pyrrolidineamide hydrochloride Rf: 0.43 (MeOH:CHCl$_3$=1:10)

We claim:

1. A compound of the formula:

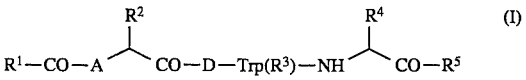

$$R^1-CO-A\overset{R^2}{\diagup}CO-D-Trp(R^3)-NH\overset{R^4}{\diagup}CO-R^5 \quad (I)$$

in which R$^3$ is hydrogen or lower alkyl,

R$^4$ is pyridyl(lower)alkyl; and

R$^1$ is C$_3$–C$_8$alkyleneamino, N,N-di(lower)alkylamino, N-lower alkyl-N-arylamino, N-lower alkyl-N-C$_3$–C$_8$cycloalkylamino, or C$_5$–C$_{10}$bicyclic alkyleneamino, R$^2$ is lower alkyl, R$^5$ is C$_3$–C$_8$alkyleneamino, N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, C$_3$–C$_8$alkyleneamino(lower)alkylamino which may be substituted by oxo, or pyridyl(lower)alkylamino, and A is lower alkylene; or R$^1$ is piperidin-1-yl, lower alkylpiperidin-1-yl, octahydroazocin-1-yl, indolin-1-yl, 1,2,3,4-tetrahydroquinolin-1-yl, N,N-di(lower)alkylamino, N-lower alkyl-N-arylamino, N-lower alkyl-N-C$_3$–C$_8$cycloalkylamino, or C$_5$–C$_{10}$bicyclic alkyleneamino, R$^2$ is lower alkyl, R$^5$ is amino or lower alkylamino, and A is lower alkylene; or R$^1$ is piperidin-1-yl, octahydroazocin-1-yl, N,N-di(lower)alkylamino, or C$_5$–C$_{10}$bicyclic alkyleneamino, R$^2$ is lower alkyl, R$^5$ is amino, lower alkylamino, N,N-di(lower)alkylamino, C$_3$–C$_8$alkyleneamino, or morpholino, and A is —NH—; or R$^1$ is hexahydro-1H-azepin-1-yl, R$^2$ is isobutyl, R$^5$ is ethylamino, and A is methylene; or R$^1$ is N-[1-(dimethylcarbamoyl)-2,2-dimethylpropyl]amino, R$^2$ is isobutyl, R$^5$ is amino, and A is —NH—; or R$^1$ is N,N-di(lower)alkylamino, 1,2,3,4-tetrahydroquinolin-1-yl, N-lower alkyl-N-arylamino, or N-lower alkyl-N-C$_3$–C$_8$cycloalkylamino, R$^2$ is lower alkyl, $R^5$ is hydroxy or CO—$R^5$ is lower alkoxycarbonyl, and
A is lower alkylene; or $R^1$ is $C_5$–$C_{10}$ bicyclic alkyleneamino,
$R^2$ is lower alkyl,
$R^5$ is hydroxy or CO—$R^5$ is lower alkoxycarbonyl, and
A is lower alkylene or —NH—; or $R^1$ is N-ethyl-N-(1-ethylpropyl)amino, N-ethyl-N-isopropylamino, N-ethyl-N-neopentylamino, or N-(1-ethylpropyl)-N-propylamino,
$R^2$ is isobutyl,
$R^5$ is hydroxy or CO—$R^5$ is lower alkoxycarbonyl, and
A is —NH—; or $R^1$ is piperidin-1-yl,
$R^2$ is isobutyl,
$R^5$ is hydroxy or CO—$R^5$ is lower alkoxycarbonyl, and
A is methylene; or $R^1$ is hexahydro-1H-azepin-1-yl,
$R^2$ is propyl,
$R^5$ is hydroxy or CO—$R^5$ is lower alkoxycarbonyl, and
A is —NH—;

or a pharmaceutically acceptable salt thereof.

2. The compound of claim 1, wherein
$R^3$ is methyl, and
$R^4$ is 2-pyridylmethyl.

3. The compound of claim 2 having the following formula:

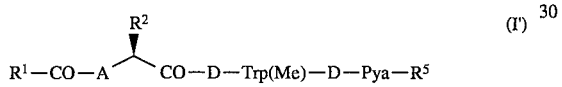  (I')

wherein $R^2$ is isobutyl, $R^5$ is pyrrolidin-1-yl, A is methylene, and $R^1$ is piperidino, hexahydro-1H-azepin-1-yl, octahydroazocin-1-yl, N-methyl-N-cyclohexylamino, N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino; or $R^2$ is isobutyl $R^5$ is pyrrolidin-1-yl, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino; or $R^2$ is isobutyl, $R^5$ is dimethylamino, A is methylene, and $R^1$ is piperidino, hexahydro-1H-azepin-1-yl, octahydroazocin-1-yl, N-methyl-N-phenylamino, N-methyl-N-cyclohexylamino, N-ethyl-N-isopropylamino, N-propyl-N-(1-ethylpropyl)amino, 3-azabicyclo[3.2.2]nonan-3-yl, N-neopentyl-N-ethylamino or N-methyl-N-(o-tolyl)amino; or $R^2$ is isobutyl, $R^5$ is dimethylamino, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan-3-yl, or N-neopentyl-N-ethylamino; or $R^1$ is hexahydro-1H-azepin-1-yl, $R^2$ is isobutyl, $R^5$ is ethylamino and A is methylene; or $R^2$ is isobutyl, $R^5$ is morpholino, A is methylene, and $R^1$ is piperidino, hexahydro-1H-azepin-1-yl, octahydroazocin-1-yl or N-methyl-N-cyclohexylamino; or $R^2$ is isobutyl, $R^5$ is morpholino, A is —NH—, and $R^1$ is piperidino, octahydroazocin-1-yl or N-ethyl-N-(1-ethylpropyl)amino; or $R^1$ is hexahydro-1H-azepin-1-yl, $R^2$ is isobutyl, A is methylene, and $R^5$ is thiomorpholino, piperidino, N',N'-dimethylhydrazino, morpholinoamino, 4-methylpiperazin-1-ylamino, ethylamino, 2-methoxyethylamino, 2-morpholinoethylamino, 3-(2-oxopyrrolidin-1-yl)-propylamino, 2-piperidinoethylamino or 2-(pyridin-2-yl)ethylamino; or $R^2$ is isobutyl, $R^5$ is amino, A is methylene, and $R^1$ is piperidino, octahydroazocin-1-yl, dipropylamino, N-methyl-N-butylamino, N-ethyl-N-butylamino, N-ethyl-N-isopropylamino, N-ethyl-N-(1-ethylpropyl)amino, N-propyl-N-(1-ethylpropyl)amino, 3-azabicyclo[3.2.2]nonan-3-yl, N-ethyl-N-neopentylamino, N-methyl-N-cyclohexylamino, N-methyl-N-phenylamino, 1,2,3,4-tetrahydroquinolin-1-yl, 4-methylpiperidino or indolin-1-yl; or $R^2$ is isobutyl, $R^5$ is amino, A is —NH—, and $R^1$ is piperidino, octahydroazocin-1-yl, N-ethyl-N-(1-ethylpropyl)amino, N-propyl-N-(1-ethylpropyl)amino, N-ethyl-N-neopentylamino, (1-dimethylcarbamoyl-2,2-dimethylpropyl)amino or 3-azabicyclo[3.2.2]nonan-3-yl;

$R^2$ is isobutyl, $R^5$ is methylamino, A is —NH—, and R is piperidino, octahydroazocin-1-yl, N-ethyl-N-neopentylamino or 3-azabicyclo[3.2.2]nonan-3-yl; or $R^2$ is isobutyl, $R^5$ is methylamino, A is methylene, and $R^1$ is piperidino, octahydroazocin-1-yl or N-methyl-N-cyclohexylamino;

$R^2$ is isobutyl, $R^5$ is hydroxy, A is methylene, and $R^1$ is piperidino, N-ethyl-N-isopropylamino, N-propyl-N-(1-ethylpropyl)amino, N-ethyl-N-(1-ethylpropyl)amino or 3-azabicyclo[3.2.2]nonan-3-yl; or $R^2$ is isobutyl, $R^5$ is hydroxy, A is —NH—, and $R^1$ is N-ethyl-N-isopropylamino, N-propyl-N-(1-ethylpropyl)amino, N-ethyl-N-(1-ethylpropyl)amino or 3-azabicyclo[3.2.2]nonan-3-yl; or $R^1$ is hexahydro-1H-azepin-1-yl, $R^2$ is propyl, $R^5$ is hydroxy and A is —NH—; or $R^2$ is isobutyl, $R^5$ is ethoxy, A is methylene, and $R^1$ is piperidino, N-methyl-N-cyclohexylamino, N-methyl-N-phenylamino, N-ethyl-N-isopropylamino, N-propyl-N-(1-ethylpropyl)amino, N-ethyl-N-(1-ethylpropyl)amino, 3-azabicyclo[3.2.2]nonan-3-yl or 1,2,3,4-tetrahydroquinolin-1-yl; or $R^2$ is isobutyl, $R^5$ is ethoxy, A is —NH—, and $R^1$ is N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino; or $R^1$ is hexahydro-1H-azepin-1-yl, $R^2$ is propyl, $R^5$ is ethoxy and A is —NH—.

4. The compound of claim 3, wherein
$R^2$ is isobutyl, $R^5$ is pyrrolidin-1-yl, A is methylene, and $R^1$ is piperidino, hexahydro-1H-azepin-1-yl, octahydroazocin-1-yl, N-methyl-N-cyclohexylamino, N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino.

5. The compound of claim 3, wherein
$R^2$ is isobutyl R is pyrrolidin-1-yl, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino.

6. The compound of claim 3, wherein
$R^2$ is isobutyl, $R^5$ is dimethylamino, A is methylene, and $R^1$ is piperidino, hexahydro-1H-azepin-1-yl, octahydroazocin-1-yl, N-methyl-N-phenylamino, N-methyl-N-cyclohexylamino, N-ethyl-N-isopropylamino, N-propyl-N-(1-ethylpropyl)amino, 3-azabicyclo[3.2.2]nonan-3-yl, N-neopentyl-N-ethylamino or N-methyl-N-(o-tolyl)amino.

7. The compound of claim 3, wherein
$R^2$ is isobutyl, $R^5$ is dimethylamino, A is —NH—, and $R^1$ is piperidino, octahydroazocin-1-yl, N-ethyl-N-isopropylamino, N-propyl-N-(1-ethylpropyl)amino, N-ethyl-N-(1-ethylpropyl)amino, 3-azabicyclo[3.2.2]nonan-3-yl, or N-neopentyl-N-ethylamino.

8. The compound of claim 3, wherein
$R^2$ is isobutyl, $R^5$ is ethylamino, A is —NH—, and $R^1$ is piperidino or octahydroazocin-1-yl.

9. The compound of claim 3, wherein
$R^2$ is isobutyl, $R^5$ is morpholino, A is methylene, and $R^1$ is piperidino, hexahydro-1H-azepin-1-yl, octahydroazocin-1-yl or N-methyl-N-cyclohexylamino.

10. The compound of claim 3, wherein
$R^2$ is isobutyl, $R^5$ is morpholino, A is —NH—, and $R^1$ is piperidino, octahydroazocin-1-yl or N-ethyl-N-(1-ethylpropyl)amino.

11. The conpound of claim 3, wherein
$R^1$ is hexahydro-1H-azepin-1-yl, $R^2$ is isobutyl, A is methylene, and $R^5$ is thiomorpholino, piperidino, N',N'-dimethylhydrazino, morpholinoamino, 4-methylpiperazin-1-ylamino, ethylamino, 2-methoxyethylamino, 2-morpholinoethylamino, 3-(2-oxopyrrolidin-1-yl)propylamino, 2-piperidinoethylamino or 2-(pyridin-2-yl)ethylamino.

12. The compound of claim 3, whrerein
$R^2$ is isobutyl, $R^5$ is amino, A is methylene, and $R^1$ is piperidino, octahydroazocin-1-yl, dipropylamino, N-methyl-N-butylamino, N-ethyl-N-butylamino, N-ethyl-N-isopropylamino, N-ethyl-N-(1-ethylpropyl)amino, N-propyl-N-(1-ethylpropyl)amino, 3-azabicyclo[3.2.2]nonan-3-yl, N-ethyl-N-neopentylamino, N-methyl-N-cyclohexylamino, N-methyl-N-phenylamino, 1,2,3,4-tetrahydroquinolin-1-yl, 4-methylpiperidino or indolin-1-yl.

13. The compound of claim 3, wherein
$R^2$ is isobutyl, $R^5$ is amino, A is —NH—, and $R^1$ is piperidino, octahydroazocin-1-yl, N-ethyl-N-(1-ethylpropyl)amino, N-propyl-N-(1-ethylpropyl)amino, N-ethyl-N-neopentylamino, (1-dimethylcarbamoyl-2,2-dimethylpropyl)amino or 3-azabicyclo[3.2.2]nonan-3-yl.

14. The compound of claim 3, wwherein
$R^2$ is isobutyl, $R^5$ is methylamino, A is —NH—, and $R^1$ is piperidino, octahydroazocin-1-yl, N-ethyl-N-neopentylamino or 3-azabicyclo[3.2.2]nonan-3-yl.

15. The compound of claim 3, wherein
$R^2$ is isobutyl, $R^5$ is methylamino, A is methylene, and $R^1$ is piperidino, octahydroazocin-1-yl or N-methyl-N-cyclohexylamino.

16. The compound of claim 3, wherein
$R^2$ is isobutyl, $R^5$ is hydroxy, A is methylene, and $R^1$ is piperidino, N-ethyl-N-isopropylamino, N-propyl-N-(1-ethylpropyl)amino, N-ethyl-N-(1-ethylpropyl)amino or 3-azabicyclo[3.2.2]nonan-3-yl.

17. The compound of claim 3, wherein
$R^2$ is isobutyl, $R^5$ is hydroxy, A is —NH—, and $R^1$ is N-ethyl-N-isopropylamino, N-propyl-N-(1-ethylpropyl)amino, N-ethyl-N-(1-ethylpropyl)amino or 3-azabicyclo[3.2.2]nonan-3-yl.

18. The compound of claim 3, wherein
$R^1$ is hexahydro-1H-azepin-1-yl, $R^2$ is propyl, $R^5$ is hydroxy and A is —NH—.

19. The compound of claim 3, wherein
$R^2$ is isobutyl, $R^5$ is ethoxy, A is methylene, and $R^1$ is piperidino, N-methyl-N-cyclohexylamino, N-methyl-N-phenylamino, N-ethyl-N-isopropylamino, N-propyl-N-(1-ethylpropyl)amino, N-ethyl-N-(1-ethylpropyl)amino, 3-azabicyclo[3.2.2]nonan-3-yl or 1,2,3,4-tetrahydroquinolin-1-yl.

20. The compound of claim 3, wherein
$R^2$ isobutyl, $R^5$ is ethoxy, A is —NH—, and $R^1$ is N-ethyl-N-isopropylamino, N-propyl-N-(1-ethylpropyl)amino, N-ethyl-N-(1-ethylpropyl)amino, 3-azabicyclo[3.2.2]nonan-3-yl or N-neopentyl-N-ethylamino.

21. The compound of claim 3, wherein
$R^1$ is hexahydro-1H-azepin-1-yl, $R^2$ is propyl, $R^5$ is ethoxy and A is —NH—.

22. A process for the preparation of a compound of the formula:

$$R^1-CO-A\overset{R^2}{\diagup}CO-D-Trp(R^3)-NH\overset{R^4}{\diagup}CO-R^5 \quad (I)$$

in which $R^3$ is hydrogen or lower alkyl, $R^4$ is pyridyl(lower)alkyl; and $R^1$ is $C_3-C_8$alkyleneamino, N,N-di(lower)alkylamino, N-lower alkyl-N-arylamino, N-lower alkyl-N-$C_3-C_8$cycloalkylamino, or $C_5-C_{10}$bicyclic alkyleneamino, $R^2$ is lower alkyl, $R^5$ is $C_3-C_8$alkyleneamino, N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, $C_3-C_8$alkeneamino(lower)alkylamino which may be substituted by oxo, or pyridyl(lower)alkylamino, and A is lower alkylene; or $R^1$ is piperidin-1-yl, lower alkylpiperidin-1-yl, octahydroazocin-1-yl, indolin-1-yl, 1,2,3,4-tetrahydroquinolin-1-yl, N,N-di(lower)alkylamino, N-lower alkyl-N-arylamino, N-lower alkyl-N-$C_3-C_8$cycloalkylamino, or $C_5-C_{10}$bicyclic alkyleneamino, $R^2$ is lower alkyl, $R^5$ is amino or lower alkylamino, and A is lower alkylene; or $R^1$ is piperidin-1-yl, octahydroazocin-1-yl, N,N-di(lower)alkylamino, or $C_5-C_{10}$bicyclic alkyleneamino, $R^2$ is lower alkyl, $R^5$ is amino, lower alkylamino, N,N-di(lower)alkylamino, $C_3-C_8$alkyleneamino, or morpholino, and A is —NH—; or $R^1$ is hexahydro-1H-azepin-1-yl, $R^2$ is isobutyl, $R^5$ is ethylamino, and A is methylene; or $R^1$ is N-[1-(dimethylcarbamoyl)- 2,2-dimethylpropyl]amino, $R^2$ is isobutyl, $R^5$ is amino, and A is —NH—; or $R^1$ is N,N-di(lower)alkylamino, 1,2,3,4-tetrahydroquinolin-1-yl, N-lower alkyl-N-arylamino, or N-lower alkyl-N-$C_3-C_8$cycloalkylamino, $R^2$ is lower alkyl,
$R^5$ is hydroxy or CO—$R^5$ is lower alkoxycarbonyl, and
A is lower alkylene; or
$R^1$ is $C_5$–$C_{10}$bicyclic alkyleneamino,
$R^2$ is lower alkyl,
$R^5$ is hydroxy or CO—$R^5$ is lower alkoxycarbonyl, and
A is lower alkylene or —NH—; or
$R^1$ is N-ethyl-N-(1-ethylpropyl)amino, N-ethyl-N-isopropylamino, N-ethyl-N-neopentylamino, or N-(1-ethylpropyl)-N-propylamino,
$R^2$ is isobutyl,
$R^5$ is hydroxy or CO—$R^5$ is lower alkoxycarbonyl, and
A is —NH—; or
$R^1$ is piperidin-1-yl,
$R^2$ is isobutyl,
$R^5$ is hydroxy or CO—$R^5$ is lower alkoxycarbonyl, and
A is methylene; or
$R^1$ is hexahydro-1H-azepin-1-yl,
R is propyl,
$R^5$ is hydroxy or CO—$R^5$ is lower alkoxycarbonyl, and
A is —NH—;
or a salt thereof, which comprises (a) reacting a compound of the formula:

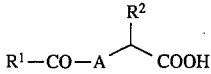

(II)

wherein $R^1$, $R^2$ and A are each as defined above or its reactive derivative at the carboxy group or a salt thereof, with a compound of the formula:

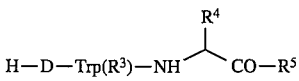

(III)

wherein $R^3$, $R^4$ and $R^5$ are each as defined above or its reactive derivative at the amino group, or a salt thereof, to give a compound of the formula:

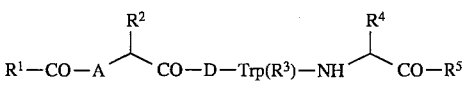

(I)

wherein $R^1$, $R^2$, $R^3$, $R^4$, $R^5$ and A are each as defined above, or a salt thereof; or (b) reacting a compound of the formula:

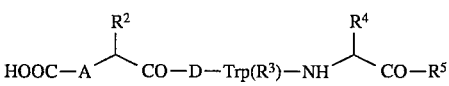

(V)

wherein $R^2$, $R^3$, $R^4$, $R^5$ and A are each as defined above, or its reactive derivative at the carboxy group, or a salt thereof, with a compound of the formula:

$R^1$—H    (IV)

wherein $R^1$ is as defined above, or its reactive derivative at the amino or imino group, or a salt thereof, to give a compound of the formula:

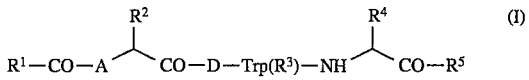

(I)

wherein $R^1$, $R^2$, $R^3$, $R^4$, $R^5$ and A are each as defined above, or a salt thereof; or (c) subjecting a compound of the formula:

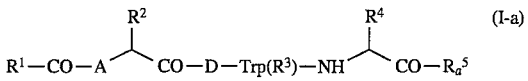

(I-a)

wherein $R^1$, $R^2$, $R^3$, $R^4$ and A are each as defined above, and CO—$R_a^5$ is protected carboxy or a salt thereof, to a removal reaction of the carboxy-protective group to give a compound of the formula:

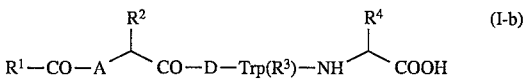

(I-b)

wherein $R^1$, $R^2$, $R^3$, $R^4$ and A are each as defined above, or a salt thereof; or (d) subjecting a compound of the formula:

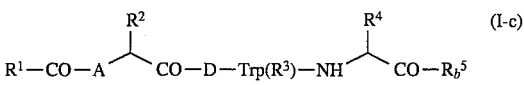

(I-c)

in which $R^1$, $R^2$, $R^3$, $R^4$ and A are each as defined above, and CO—$R_b^5$ is carboxy or protected carboxy, or a salt thereof, with a compound of the formula:

$R_c^5$—H    (XII)

in which $R_c^5$ is $C_3$–$C_8$alkyleneamino N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, $C_3$–$C_8$alkyleneamino(lower)alkylamino which may be substituted by oxo, pyridyl(lower)alkylamino, amino or lower alkylamino, to give a compound of the formula:

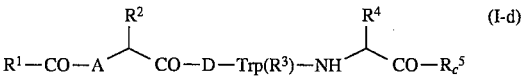

(I-d)

in which $R^1$, $R^2$, $R^3$, $R^5$ and A are each as defined above, or a salt thereof.

23. A pharmaceutical composition which comprises a compound of claim 1 or a pharmaceutically acceptable salt thereof and a pharmaceutically acceptable carrier or excipient.

24. A method for treating endothelin mediated diseases which comprises administering a compound of claim 1 or pharmaceutically acceptable salts thereof to human being or animals.

* * * * *